US009232949B2

(12) United States Patent
Carusillo et al.

(10) Patent No.: US 9,232,949 B2
(45) Date of Patent: Jan. 12, 2016

(54) SURGICAL SAGITTAL SAW WITH A DRIVE ASSEMBLY CAPABLE OF DISPLACING THE ATTACHED BLADE IN A CROSSED LOOP PATTERN

(71) Applicant: Stryker Corporation, Kalamazoo, MI (US)

(72) Inventors: Steven Carusillo, Kalamazoo, MI (US); James G. Walen, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 3 days.

(21) Appl. No.: 14/069,669

(22) Filed: Nov. 1, 2013

(65) Prior Publication Data

US 2014/0088600 A1    Mar. 27, 2014

Related U.S. Application Data

(63) Continuation of application No. PCT/US2012/035412, filed on Apr. 27, 2012.

(60) Provisional application No. 61/482,409, filed on May 4, 2011.

(51) Int. Cl.
    A61B 17/14    (2006.01)
    A61B 17/32    (2006.01)

(52) U.S. Cl.
    CPC ............... *A61B 17/148* (2013.01); *A61B 17/14* (2013.01); *A61B 17/32002* (2013.01); *A61B 17/141* (2013.01)

(58) Field of Classification Search
    CPC ........... A61B 17/148; A61B 17/32002; B23D 49/165
    See application file for complete search history.

(56) References Cited

U.S. PATENT DOCUMENTS

| 3,977,289 | A | * | 8/1976 | Tuke ............................... 83/835 |
| 3,978,862 | A |   | 9/1976 | Morrison |
| 4,836,069 | A |   | 6/1989 | Dinh et al. |
| 5,201,749 | A | * | 4/1993 | Sachse et al. ................. 606/177 |
| 2007/0016238 | A1 | | 1/2007 | Marietta |
| 2008/0027449 | A1 | | 1/2008 | Gundlapalli et al. |

OTHER PUBLICATIONS

"ISA Search Report & Written Opinion of PCT/US2012/035412", dated Oct. 8, 2012.

* cited by examiner

*Primary Examiner* — Andrew Yang

(57) ABSTRACT

A saw for pivoting a blade in a sagittal plane. The saw includes a drive assembly with at least one drive member. The drive assembly is configured to both reciprocate the blade in the sagittal plane and to simultaneously pivot the blade around an axis that extends through the sagittal plane. The drive assembly is configured to reciprocate and pivot the blade at different frequencies. Consequently the teeth (186) of the blade travel in a loop pattern that crosses itself.

38 Claims, 27 Drawing Sheets

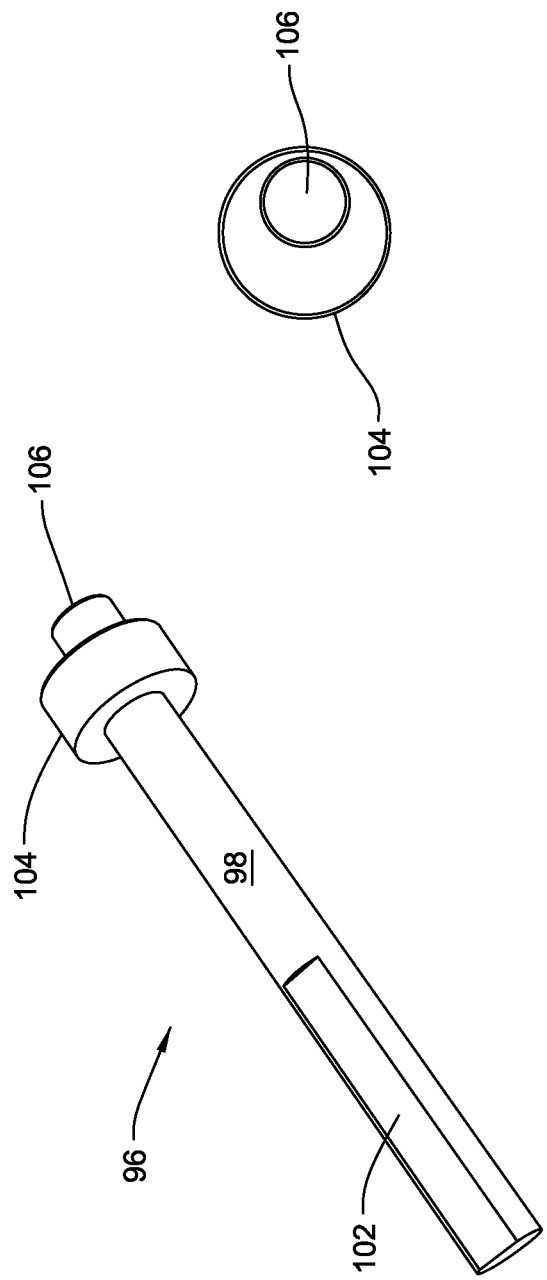

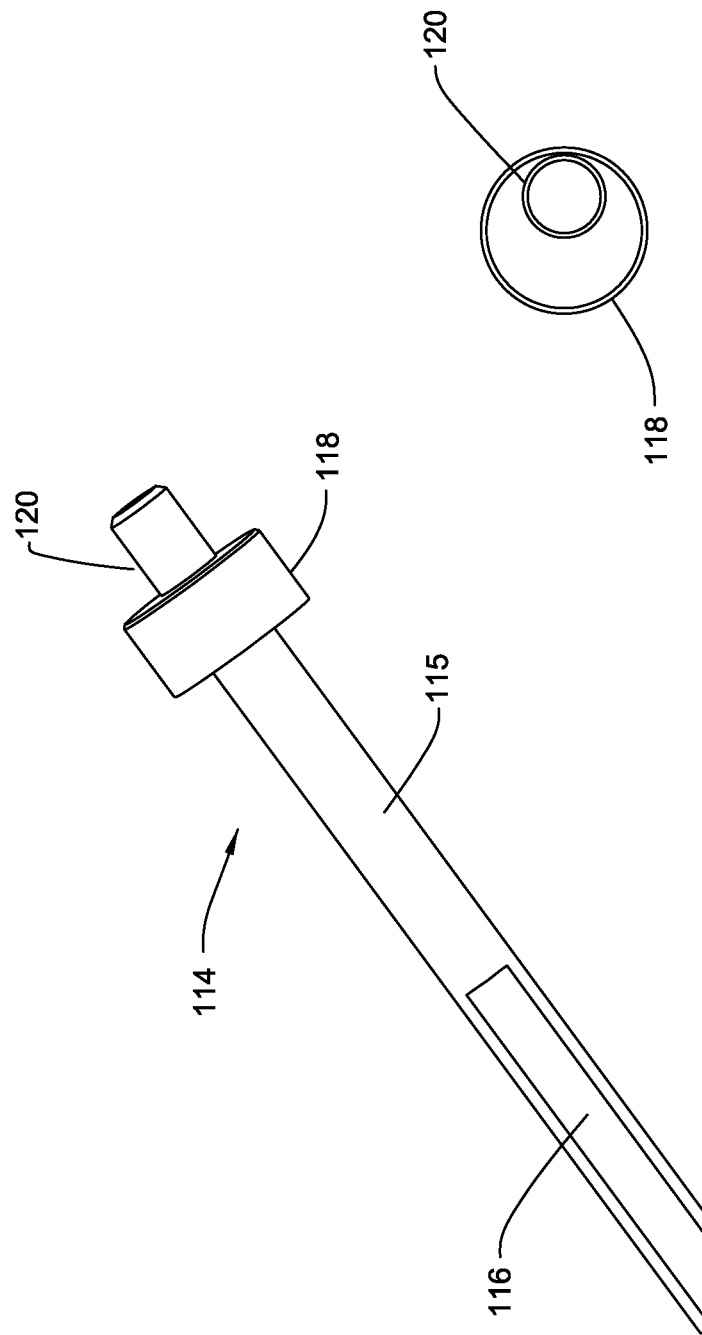

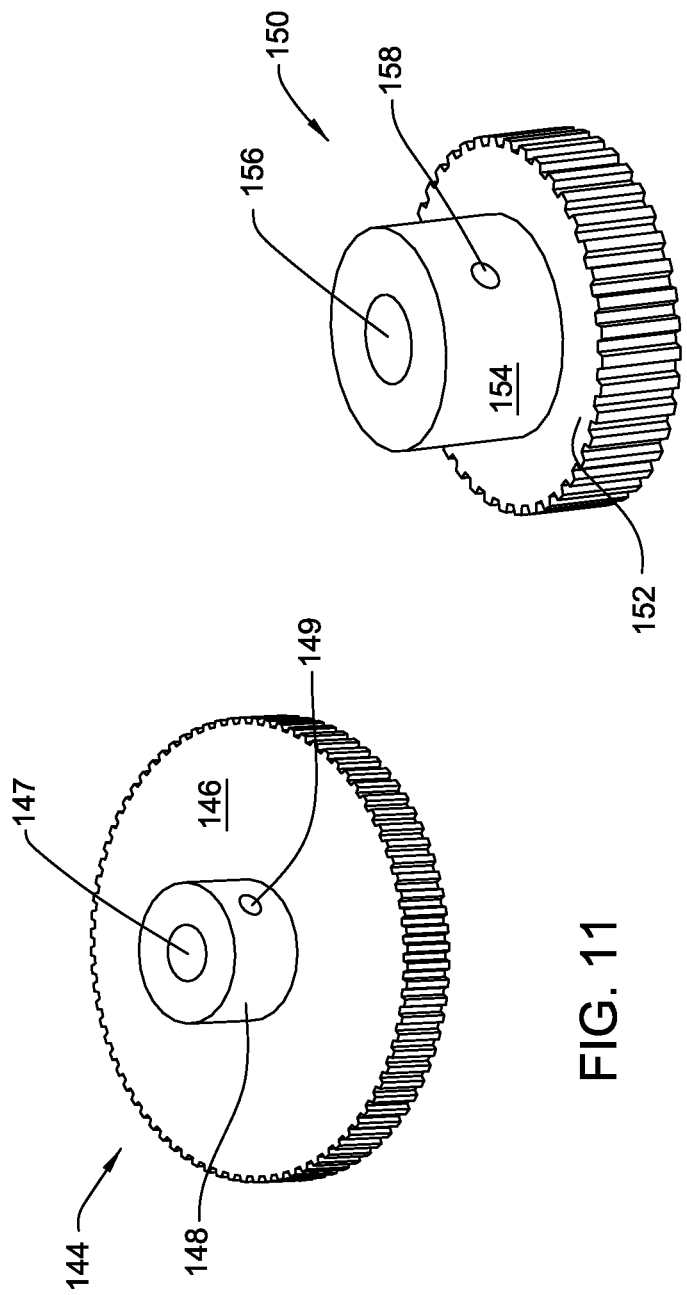

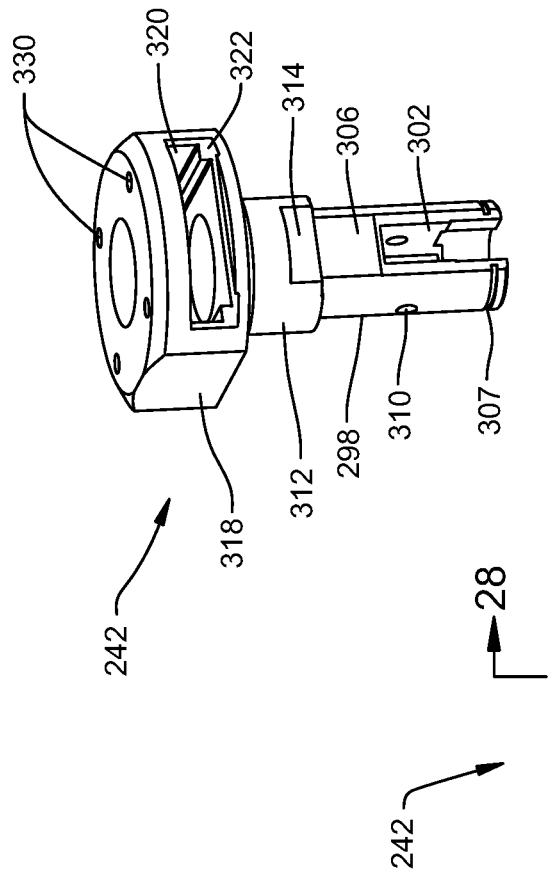
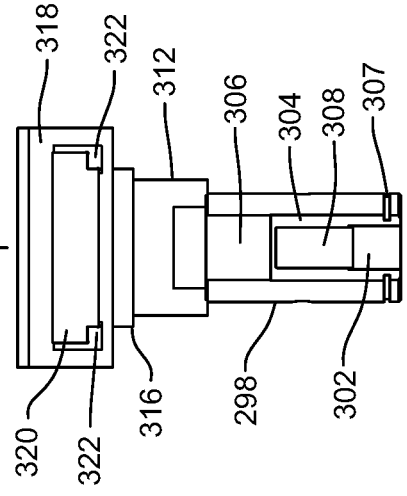
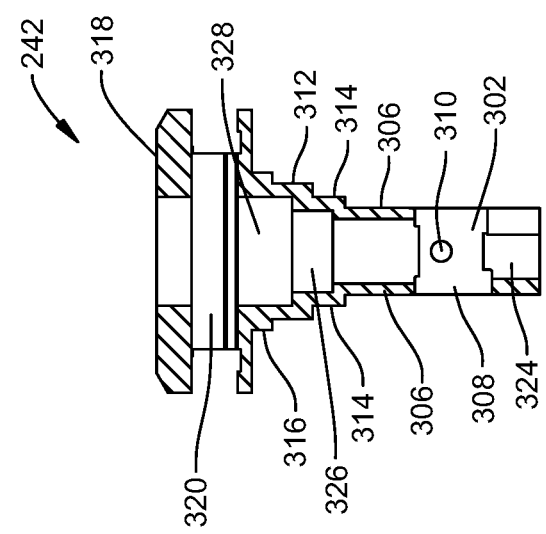
FIG. 26
FIG. 27
FIG. 28

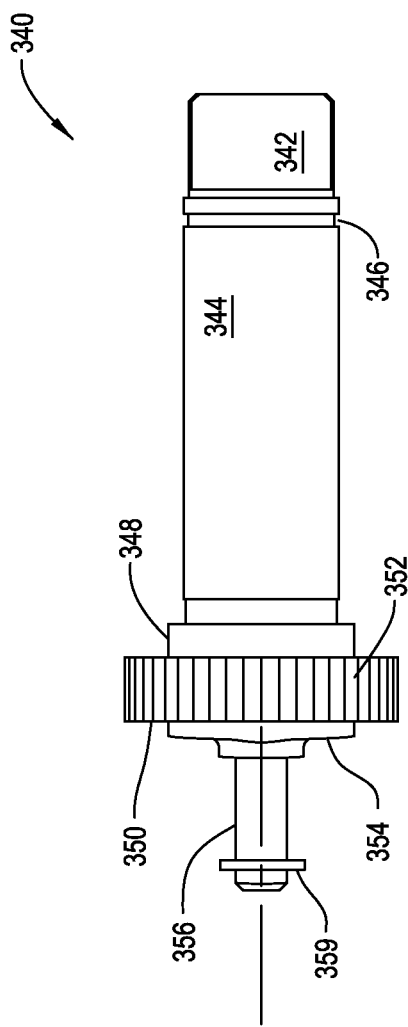
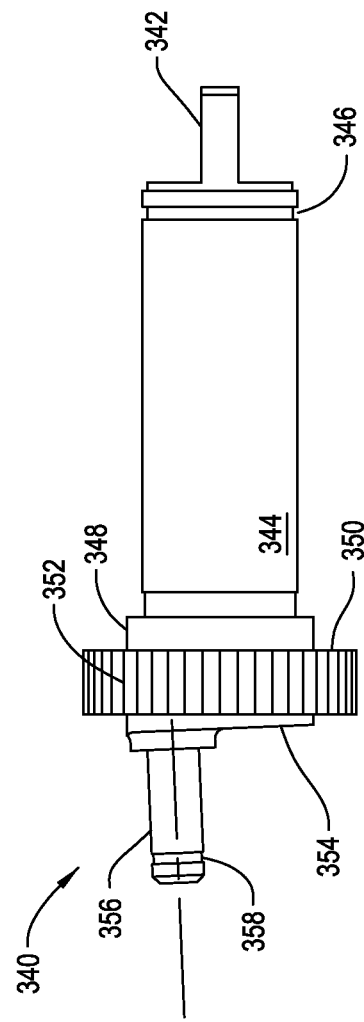
FIG. 29
FIG. 30

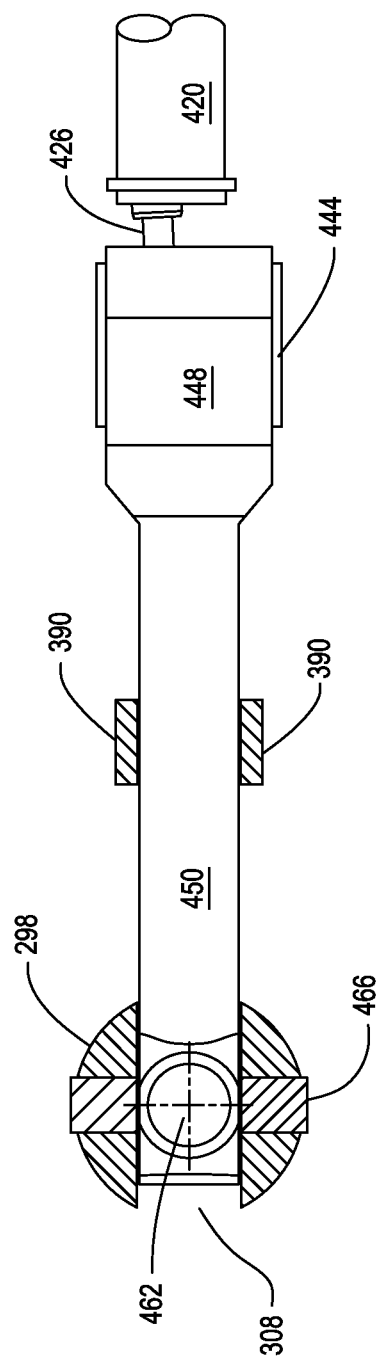

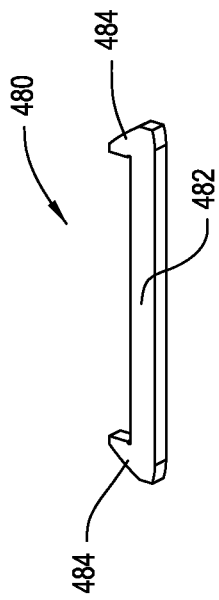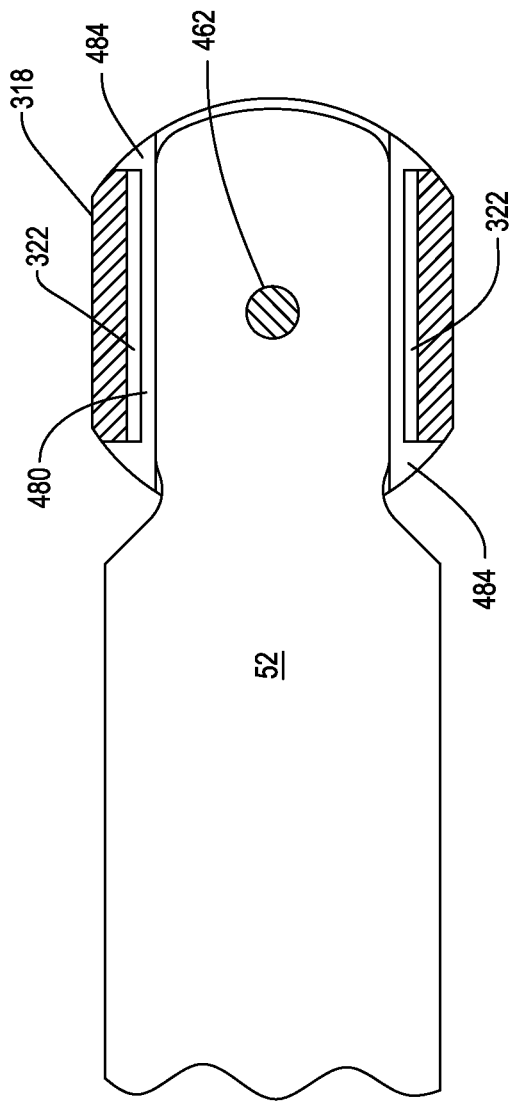
FIG. 41
FIG. 40

SURGICAL SAGITTAL SAW WITH A DRIVE ASSEMBLY CAPABLE OF DISPLACING THE ATTACHED BLADE IN A CROSSED LOOP PATTERN

RELATIONSHIP TO PRIORITY APPLICATIONS

This application is a continuation of PCT App. No. PCT/US2012/035412 filed 27 Apr. 2012. PCT App. No. PCT/US2012/035412 is a non-provisional of U.S. Prov. Pat. App. No. 61/482,409 filed 4 May 2011. The contents of the above-identified applications from which this application claims priority are incorporated herein by reference.

FIELD OF THE INVENTION

This invention relates generally to a surgical sagittal saw. More particularly, this invention is directed to a surgical sagittal saw capable of actuating the blade attached to the saw in crossed loop pattern such as a figure eight pattern.

BACKGROUND OF THE INVENTION

A sagittal saw is a powered surgical tool often used in an orthopedic surgical procedure. A sagittal saw includes a body that houses a motor and the complementary control circuit that regulates the actuation of the motor. Extending forward, distally, from the body, is a planar saw blade. The most forward end of the saw blade is formed with teeth for cutting hard tissue, the bone, against which the blade is applied. A drive mechanism internal to the housing transfers the power developed by the motor to the blade. The drive mechanism of a conventional sagittal saw converts the rotary motion produced by the output shaft of the motor to the blade so that the distal end of the blade moves back-and-forth along an arc. This arc is in the plane in which the blade is aligned. Consequently, when a sagittal saw is actuated, the blade teeth move in a back-and-forth pattern against the tissue to which the teeth are applied. As a consequence of this motion and the forward pressure applied by the surgeon holding the saw, the teeth cut and separate the hard tissue or bone.

Conventional sagittal saws work reasonably well for the purposes for which they are intended. There is, however, a disadvantage associated with the conventional sagittal saw. This disadvantage is understood to by reference to FIGS. 1A and 1B. Initially it should be understood that as the distal end of a blade 40 sweeps against the bone to be cut, the blade teeth, as intended, plow into the this face of uncut bone. This plowing action scrapes the uncut bone away from the bone face. This scraped bone forms a mass of bone remnants, a collection of bone dust and bone chips. As mentioned above, a conventional sagittal saw causes the distal end of the attached blade to move in a back and forth pattern along an arc. In FIG. 1A, blade head 40 is shown sweeping to the right as represented by curved arrow 42. As a consequence the right side of the teeth, for example, tooth 44 is the side of the tooth that that plows into the bone and creates bone remnants 45. These bone chips accumulate in the space between the left side of tooth 44 and the right side of tooth 46. FIG. 1B, represents the return phase of the complete cycle of the displacement of the blade head 40. Blade head 40 sweeps to the left as represented by curved arrow 48. In this phase of the displacement of the distal end of the blade it is the left sides of the teeth that plow into the bone. As a consequence of this plowing action tooth 46 generates additional bone remnants 45 that fill the space between teeth 44 and 46.

It should therefore be appreciated that, when cutting bone, a large volume of bone remnants can rapidly accumulate between the blade teeth. During the cutting process, the blade is sandwiched top to bottom between two sections of uncut bone. Consequently the trapped bone chips are not simply, upon filling the spaces between the teeth, discharged upwardly or downwardly out of the kerf being cut in the bone. Further, it should be understood that often the arc across which any individual tooth sweeps typically has a length of 1.3 cm or less and more often 0.8 cm or less. The blade itself may have a width across that is 3 cm or less and often 2.5 cm or less. Micro sagittal blades have a width across the blade of 1.0 cm or less. Often these blades are positioned in bone so as to form kerfs that, until the bone is completely cut across are bordered on one if not both sides by uncut bone. This limits the ability of the accumulated bone chips from being discharged outwardly from the sides of the kerf being cut.

Thus, it should be appreciated that when cutting bone, especially large bones such as femur or tibia, in a relatively short amount of time, a significant volume of bone remnants can accumulate around the teeth of a surgical sagittal saw blade. These bone remnants impede the ability of the blade teeth to press into and cut away the remaining bone.

The Applicants' Assignee's U.S. Pat. No. 3,978,862 suggests one potential means of reducing the build up of bone chips in the kerf formed by a sagittal saw. This document discloses a saw capable of simultaneously pivoting a blade back and forth and moving the blade longitudinally within the blade mount. The saw of this invention is designed so that there is a 1:1 ratio in the right-to-left and back to right pivoting cycle of the blade and the front-to-right and back to front longitudinal displacement. In a single cycle, the blade head travels in an elliptical path. When this type of saw is actuated, in separate phases of the pivoting cycle, the attached blade moves both forward and away from the face of the bone against which the blade teeth are pressed.

Consequently, when a blade is actuated using this type of saw, the blade teeth travel in one direction around what can be described as a loop. In each cycle in which the blade is actuated, the blade, when it is most distal position is moved in one direction, to the right or to the left, of the extension of the longitudinal axis of the saw. As a result, when the blade is pressed against the surface of the bone the blade is intended to cut, the blade pulls in the direction, right or left, in which the blade is cycled. A surgeon using this blade must therefore apply a counterforce to counteract this biasing pull.

SUMMARY OF THE INVENTION

This invention is related to a new and useful surgical sagittal saw. The saw of this invention has a drive assembly that drives the attached saw blade in a closed loop pattern wherein the loop through which the blade teeth travels crosses over itself.

The drive assembly of this invention includes drive assembly with actuating members that engage and displace the blade attached to the saw. One of the actuating members pivots the blade so that, the distal end of the blade pivots to the right and left of an axis that extends through the plane of the blade. The second actuating member reciprocates the blade distally and proximally so that the blade engages in translation motion along an extension of the longitudinal axis through the blade. This axis is in the plane in which the blade is disposed.

The blade actuating members operate do not operate at a 1:1 cycle rate. Instead, the blade actuating members are configured so that, during the time the blade engages in one cycle, it undergoes a different number of front to rear and back to front pivoting cycles. As a consequence of the blade engaging in pivotal and reciprocating motions that are at different frequencies, the blade, more particularly, a given blade tooth, undergoes, travels along a path that can be described as a crossed loop. That is as the tooth is displaced, at least once in path of the tooth the tooth crosses over a location the tooth previously traveled in tracing out the loop of travel.

In one version of the invention, the blade actuating members are arranged so that for every one cycle of the actuating member that pivots the blade, the actuating member that reciprocates the blade undergoes two cycles. This version of the invention may further be configured so that as the pivoting actuating member pivots the blade to the right (or left) from a position in line with the saw longitudinal axis to the furthest outward location, the reciprocating actuating member causes the blade to move forwardly and the rearwardly. Then, as the pivoting actuating member pivots the blade to the left (or right) back to the axially in line position, the reciprocating actuating member causes the blade to move rearwardly and then forwardly. Thus during this operation, the pivoting actuating member will have displaced the blade through one-half of a complete pivoting cycle while the reciprocating actuating member displaced the blade for a complete reciprocation cycle. Once the blade returns to the start position, the rest of the pivoting cycle is completed while the reciprocation cycle is fully repeated. During this displacement of the blade, a single tooth travels a closed loop pattern that is in the form of a figure-eight. The loop crosses at a point in line with the longitudinal axis extension of the saw.

In some versions of the invention, the drive assembly actuating members are both pins. Each pin seats in a separate complementary opening in the blade. The pins engage in their repetitive motions at different frequencies. One pin pivots the blade and the second pin reciprocates the blade.

In some versions of the invention, the drive assembly actuating members includes a moving blade mount and a moving pin. The blade mount is the structural member that holds the blade to the saw. The moving pin is attached to the blade mount to both move with the blade mount and engage in its own movement relative to the blade mount. For example, in one embodiment of this version of the blade mount pivots to the right and left. The moving pin reciprocates within the blade mount. The blade mount is designed to removably hold the blade. More particularly, when the blade is fixed to the blade mount, the blade is constrained from lateral and vertical motion and is able to move longitudinally. One set of drive components pivot the blade mount so as to cause the like displacement of the blade. A second set of drive members reciprocate the pin distally and proximally. When this version of the sagittal saw of this invention is actuated, the blade mount pivots the blade while the pin causes the blade to reciprocate distally and proximally.

BRIEF DESCRIPTION OF THE DRAWINGS

The invention is pointed out with particularity in the claims. The above and further features and advantages of this invention are understood by reference to the following Detailed Description taken in conjunction with the accompanying drawings in which:

FIG. 7 is a perspective view of the distally located drive shaft internal to the drive head;

FIG. 8 is a plan view of the top of the drive shaft of FIG. 7;

FIG. 9 is a perspective view of the proximally located drive shaft;

FIG. 10 is a plan view of the top of the drive shaft of FIG. 9;

FIG. 11 is a perspective view of the gear attached to the proximal of the two drive shafts internal to the drive head;

FIG. 12 is a perspective view of the gear attached to the distal of the two drive shafts internal to the drive head;

FIG. 26 is a perspective view of the rear, proximally directed portion of the blade mount of the surgical sagittal saw of FIG. 17;

FIG. 27 is a pan view of the rear of blade mount of FIG. 26;

FIG. 28 is a cross sectional view of the blade mount taken along line 28-28 of FIG. 27;

FIG. 29 is a first side view of the first drive shaft of the surgical sagittal saw of FIG. 17;

FIG. 30 is a second side view of the drive shaft of FIG. 29 after the shaft has rotated 90';

FIG. 39 is a top plan and partial cross sectional view showing the relationship of the toggle link to the second drive shaft, the drive link and the blade mount;

FIG. 40 is a plan and partial cross sectional view of how within the blade mount head the saw blade is seated between wear bars and coupled to the toggle link;

FIG. 41 is a perspective view of one of the wear bars internal to the blade mount;

DETAILED DESCRIPTION

I. First Embodiment

Figure 1A:
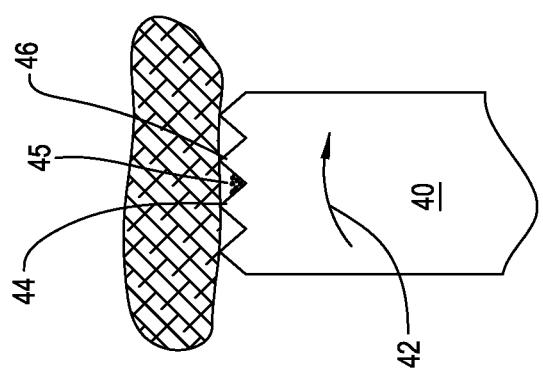
FIGS. 1A and 1B depict how bone chip can build up around the teeth of sagittal saw blade when the blade is actuated in conventional pivoting movement.
Figure 1B:
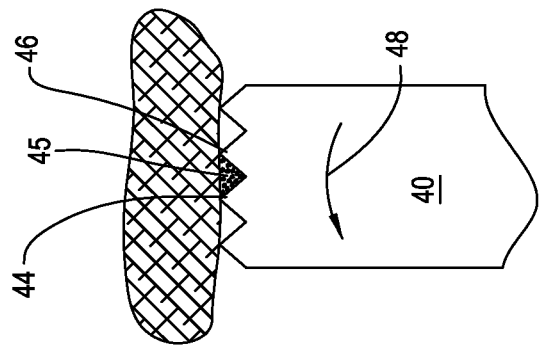
Figure 2:
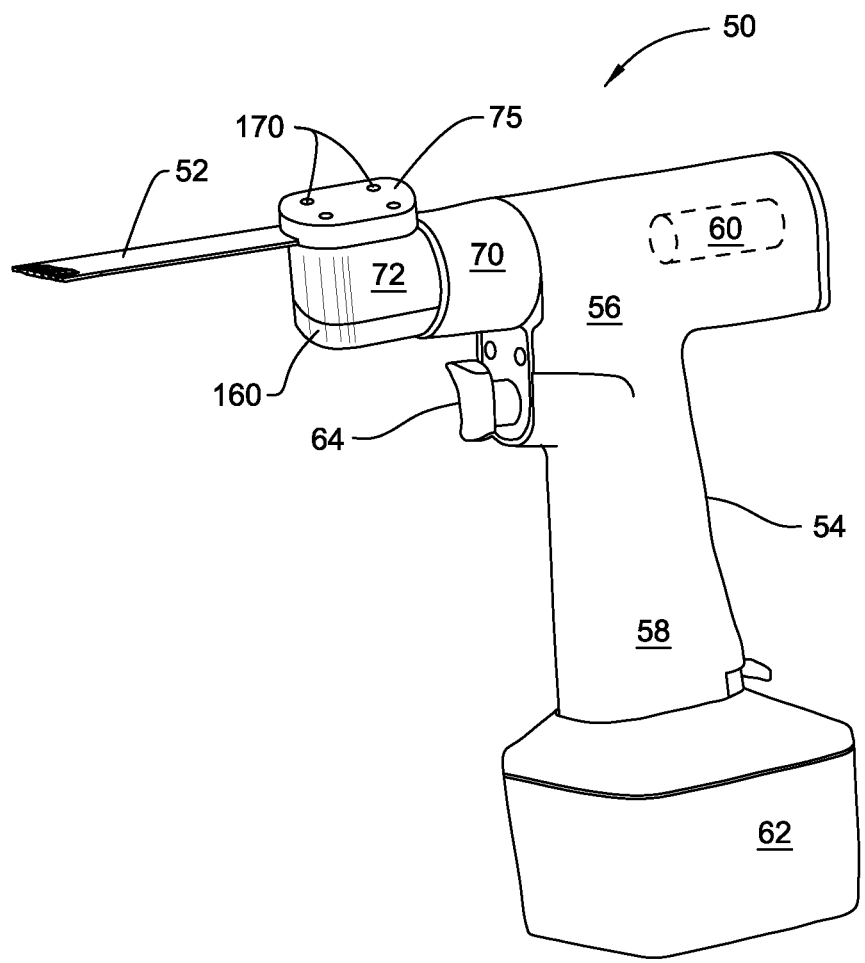
FIG. 2 is a perspective view of a surgical sagittal saw of this invention.

FIG. 2 illustrates a surgical sagittal saw 50 constructed in accordance with this invention for oscillating a saw blade 52. Saw 50 includes a body 54. In the particular version of the invention, body 54 is generally pistol shaped. Saw body 54 has a generally barrel shaped head 56. A hand grip 58, also part of body 54, extends downwardly from head 56. A motor, represented by a phantom cylinder 60, is disposed inside housing head 56. In some versions of the invention, the motor is a brushless DC motor. It should be appreciated that this is exemplary, not limiting. In the illustrated version of the invention, saw 50 is cordless tool. A battery 62 removably attached to the butt end of the hand grip 58 contains a charge for energizing the motor. Again, it should be understood that the invention is not so limited. In alternative versions of the invention, a power cord, an air line or a fluid line is connected to the body 54 for providing the power needed to actuate the motor.

A trigger 64 is moveably mounted to the saw body 54. In the illustrated version of the invention, trigger 64 extends distally forward from the hand grip 58 immediately below the head 56. ("Distal", it shall be understood means toward the surgical site to which the saw 50 is directed. "Proximal", means away from the surgical site.). A control circuit internal to the body 54, not illustrated and the structure of which is not part of this invention, monitors the actuation of the trigger 64. Based on the extent to which the trigger switch 64 is actuated, the control circuit selectively energizes the motor 60 to cause an output shaft 132 (FIG. 3) connected to the motor to rotate at the desired speed.

Figure 3:
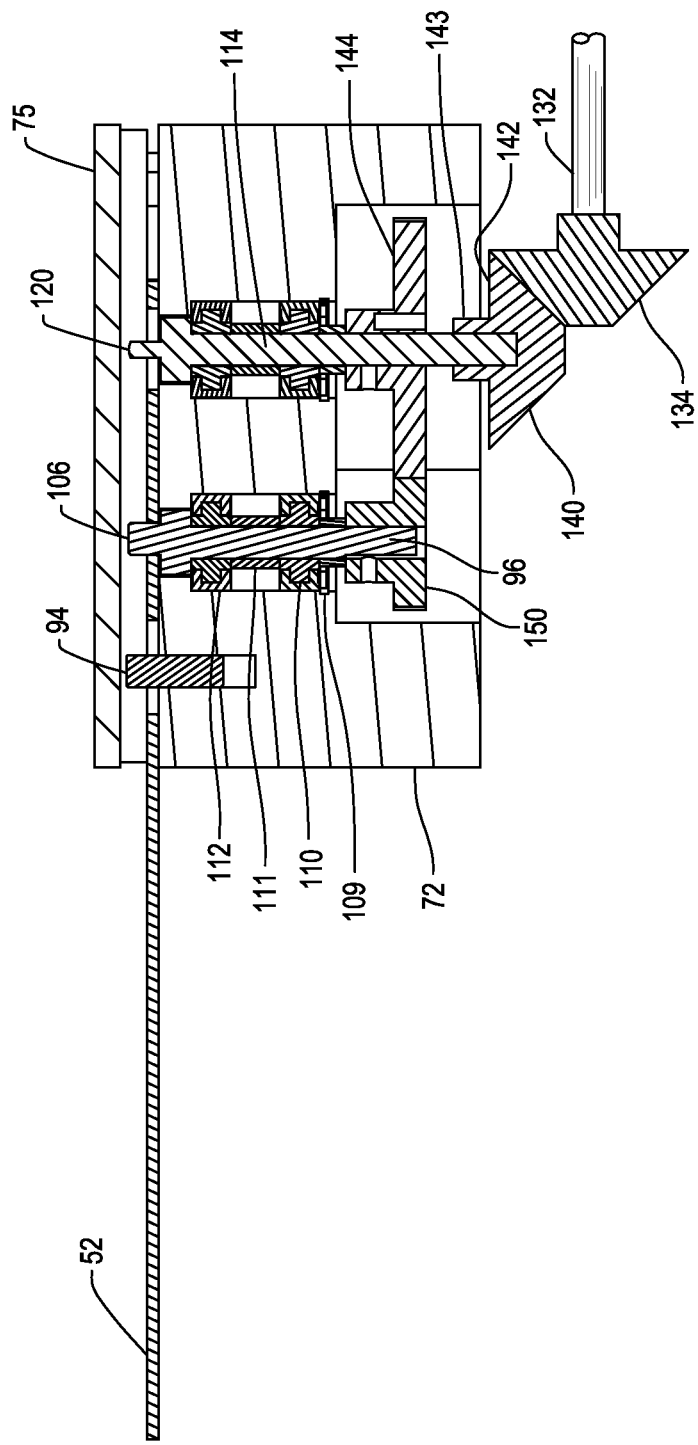
FIG. 3 is cross sectional view of the head of the drive head of the saw of FIG. 2.

A drive head 72 is located forward of housing head 56. A neck 70 located between the housing head 56 and the drive head 72 holds the drive head to the body 54. As discussed below, disposed in the drive head 72 is a drive assembly that actuates the blade 52. A cap 75 is removably fitted over the top of the drive head 72. Blade 52 is sandwiched between the drive head 72 and cap 75. The drive head 72 is in the form of a solid block. Drive head 72 is shaped to have a planar top surface 73, seen best in FIG. 4. Surface 73 is the surface of drive head 72 against which the blade 52 is seated. As seen in FIG. 3, a static pin 94 and two drive pins 106 and 120 are mounted to the drive head 72 so as to extend upwardly above head top surface 73. Static pin 94, as its name implies, is statically mounted to the drive head 72. Drive pins 106 and 120 are each mounted to the drive head so as to be able to rotate. Each drive pin 106 and 120 rotates in a circular pattern.

Figure 15:
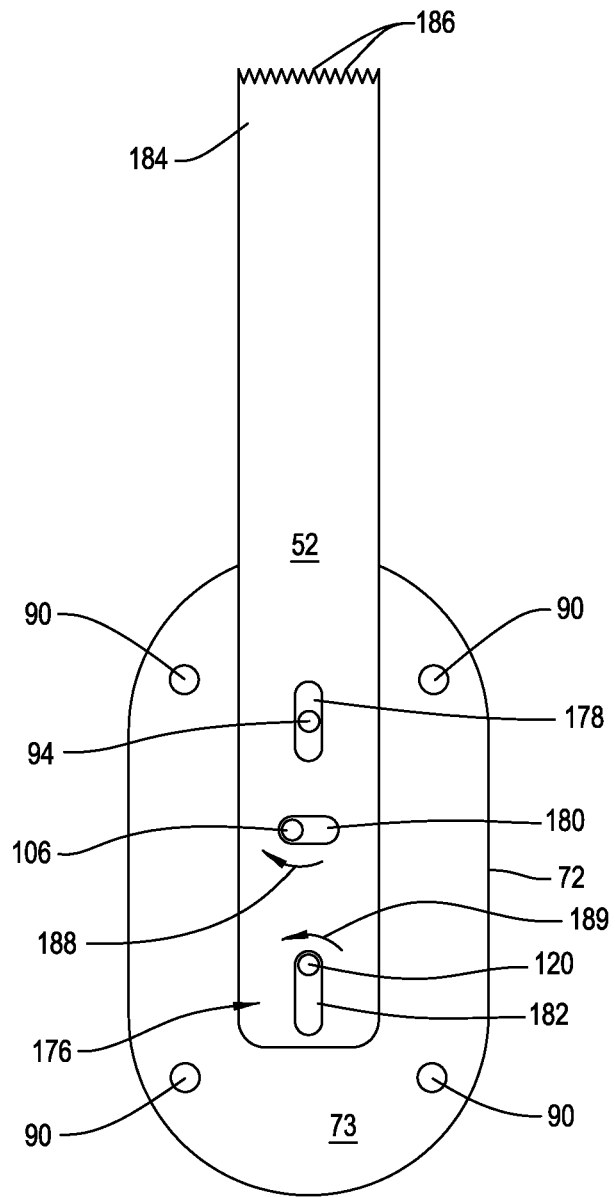
FIG. 15 is a plan view of a surgical sagittal saw blade designed for use with the saw of FIG. 1.

When the blade 52 is fitted to saw 50, each pin 94, 106 and 120 seats in a separate opening, respectively openings 178, 180 and 182 formed in the blade (FIG. 15). The actuation of the motor results in the rotation of the drive pins 106 and 120. More specifically, saw 50 of this invention is configured so that pins 106 and 120 rotate at different speeds. Owing to the difference in rotational speeds of pins 106 and 120, when the saw is actuated, the pins displace the blade so as to cause the distal end of the blade to travel in a loop pattern in which at least one segment of the loop crosses over another segment.

Figure 4:
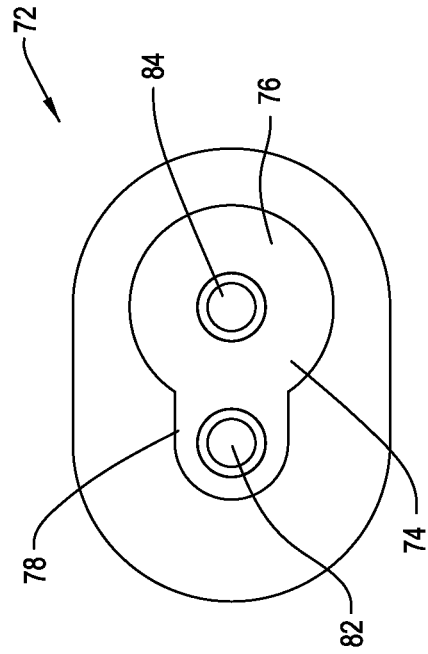
FIG. 4 is a top plan view of the drive head.
Figure 5:
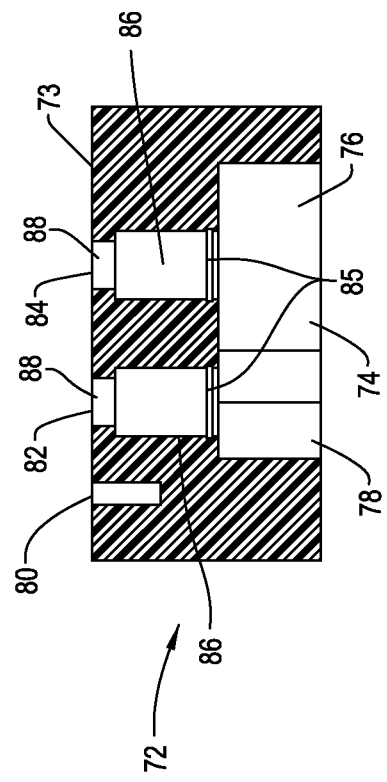
FIG. 5 is a cross sectional view of the drive head taken along line 5-5 of FIG. 4.
Figure 6:
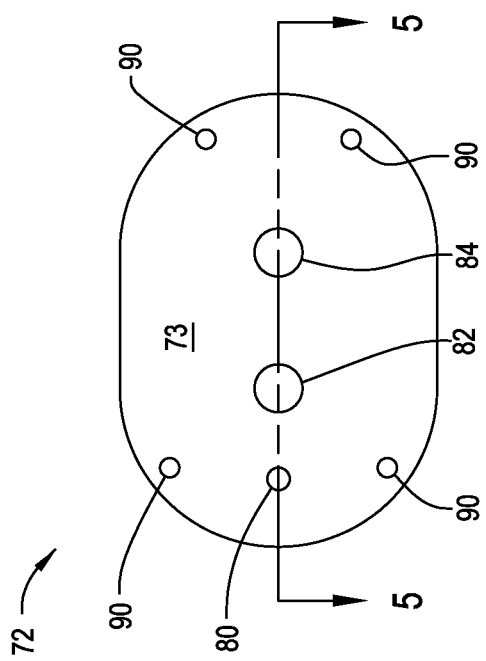
FIG. 6 is a bottom view of the drive head.

As seen in FIGS. 4-6, drive head 72 is generally in the form of an oval shaped block. The drive head 72 is formed with a keyhole shaped recess 74 that extends upwardly from the bottom surface of the head. Recess 74 is formed to have a proximal portion, portion 76, that is generally circular in cross sectional shape. The center point of the recess proximal portion 78 is on the longitudinal axis of the head 72. The recess has a distal portion 78 that is contiguous with and extends forward from proximal portion 76. Recess distal portion 78 appears in cross section to substantial subtend the outline of an oval. The major axis of the distal portion 78 is collinear with the longitudinal axis of the head. The width across the recess distal portion 78 is less than the diameter across the proximal portion 76.

Drive head 72 is further formed to have a number of bores that extend inward from top surface 73 of the head. Three of the bores are centered on the longitudinal axis of the head. The most distally located of these bores is a closed end bore, bore 80. The remaining two bores centered on the longitudinal axis of the head, bores 82 and 84, both open into recess 74. Bore 82, the distal of the two bores 82 and 84, is centered on the point around which the internal surface of the drive head 72 that defines the recess distal portion 78 curves. Bore 84 is centered on the center point around which the recess proximal portion 76 is curved. Bores 82 and 84 are multi-section bores. Each bore 82 and 84 has a top section, section 88. Bore sections 88 are the sections of bores 82 and 84 that extend immediately downward from head top surface. Each bore has a bottom section, section 86. Bore bottom sections 86 are greater in diameter than bore top sections 88. The bore bottom sections 86 are the sections of the bores 82 and 84 located between recess 74 and bore sections 88. The drive head 72 is further formed so that a groove 85 extends outwardly from the curved annual wall that defines each bore section 86. The grooves 85 are located immediately above recess 74.

The drive head 72 is further formed so that four additional closed end bores, bores 90 extend inwardly from top surface 73. Bores 90 are threaded (threading not illustrated). Two bores 90 are located adjacent each of the two opposed side edges of the top face of the drive head 72. Bores 90 are further arranged in pairs where the bores of each pair are symmetrically located around the head longitudinal axis.

Static pin 94 is press fit in drive head bore 80 so as to project above the head top surface 73.

Drive pin 106, the distal of the two drive pins, is part of a distal drive shaft 96 rotatably mounted in head bore 82. As seen in FIGS. 7 and 8, drive shaft 96 is a single piece component. Shaft 96 has a stem 98 that is generally cylindrical in shape. The drive shaft 96 is further formed so that stem 98 has a flat 102. Flat 102 extends upwardly from the bottom of stem 98 and extends approximately 20 to 40% of the overall length of the stem. The flat 102 subtends an arc that extends approximately 90 to 120° around the circumference of the stem 98. A head 104, that is coaxial with the stem 98, is located over the top of the stem 98. The head 104 is of cylindrical shape. The diameter of the head is greater than that of the stem 98. More particularly, drive shaft head 104 has a diameter less than that of the drive head bore sections 88. Thus, when the drive shaft head 104 is seated in the complementary bore head section 88, the head can freely rotate in bore 82.

Drive pin 106 extends upwardly from the top surface of shaft head 104. The drive pin 106 is the form of a cylindrically shaped boss. Distal drive shaft 96 is further shaped so that the drive pin 106 has a diameter less than that of the adjacent head 104 and so that the center axis of the drive pin 106 is laterally spaced from the common axis of stem 98 and head 104.

Two bearing assemblies 110 and 112, seen in FIG. 3, rotatably hold the distal drive shaft 96 in bottom section 86 of drive head bore 82. The inner race of each bearing assembly 110 and 112 is disposed against the shaft 98. The outer race of each assembly 110 and 112 is disposed against the adjacent cylindrical wall of the drive head that defines the bore bottom section 86. (Races not identified) A first one of the bearing assemblies, bearing assembly 110, is disposed in bore 82 immediately above groove 85. A C-shaped snap ring 109 is disposed in the grove. The inner perimeter of the snap ring 109 extends inwardly into the bore section 86. The outer race of the bottommost bearing assembly 110 seats against this exposed inner perimeter of the snap ring 109. Snap ring 109 thus holds the bearing assembly 110 in bore 82.

The second of the two bearing assemblies, bearing assembly 112, is spaced above the first described bearing assembly 110. A tube like spacer 111 is disposed around bearing shaft stem 98. More particularly, one of the annular faces of spacer 111 abuts the adjacent annular face of the inner race of bearing assembly 110. Bearing assembly 112 is disposed around the stem 98 so as to be located above spacer 111. More particularly, the downwardly directed annular face of the inner race of bearing assembly 112 is seated against the adjacent annular face of spacer 111. Spacer 111 thus holds bearing assembly 112 above bearing assembly 110. Upon assembly of saw 50 the top of shaft head 104 is located at or below drive head top surface 73, drive pin 106 projects above the top surface 73.

Drive pin 120 is part of a proximal drive shaft 114 now described by reference to FIGS. 9 and 10. Proximal drive shaft has a stem 115, a flat 116 and head 118 analogues to the corresponding features of distal drive shaft 96. The most appreciable difference between the shafts is that stem 115 and shaft 115 and flat 116 of shaft 114 are longer in length than the corresponding shaft 98 and flat 102 of distal drive shaft 96. The longitudinal axis of drive pin 120 is laterally offset from the common axis of shaft stem 115 and shaft head 118.

When the drive shaft 114 is rotatably mounted to the drive head 72, the shaft head 118 is seated in top section 88 of bore 84. More particularly, the drive shaft 114 is positioned so that the top surface of the shaft head 104 is positioned to be planar or slightly below head top surface 73. Drive pin 120 extends up above top surface 73.

A second snap ring 109, a second set of bearing assemblies 110 and 112, and a second spacer 111 rotatably hold the proximal drive shaft stem 115 in head bore 84, (snap ring, bearing assemblies and spacers not identified). This second snap ring 109 seats in the groove 85 formed in bore 84. Drive shaft 114 is rotatably mounted in drive head bore 84 so that the shaft head 118 is disposed in bore top section 88. More specifically, the top surface of drive shaft head 118 is planar or slightly below the top surface of drive head 72.

Two gears 140 and 144 are mounted to stem 115 of drive shaft 114. Gear 140, the bottommost gear, is a bevel gear. Gear 140 has a head 142 which include the teeth (not illustrated) of the gear. A neck 143, which has a diameter smaller than head 142 extends upwardly from the head. A closed end bore, not identified, extend through gear neck 143 and partially through gear head 142. This bore is shaped to slidably receive the portion of the stem 115 of drive shaft 114. A set screw extends through a threaded bore neck 143 to hold gear 140 and sets against shaft flat 116. (Set screw and bore not illustrated). The set screw thus holds gear 140 to drive shaft 114. Gear 140 is located below drive head 72.

Gear 140 meshes with a complementary bevel gear 134. Bevel gear 134 is attached to the distal end of the output shaft 132 that is connected to motor 60. (Output shaft to motor connection not shown). Output shaft 132 and gears 134 and 140 thus transfer the rotational power developed by the motor 60 to the drive assembly internal to the drive head 72 that actuates the blade 52.

FIG. 11 illustrates the second gear, gear 144 attached to the stem 115 of drive shaft 114. Gear 144 has a head 146, which is the portion of the gear formed with teeth (not identified). A neck 148, with a smaller diameter than the head 146, extends upwardly from the head. Gear head 146 and neck 148 are formed with a common bore, 147 that extends axially through the gear. Bore 147 is designed to closely receive drive shaft stem 115. A threaded bore 149 extends radially from the outer surface of neck 148 to bore 147. When saw 50 is assembled, gear 144 is positioned on shaft stem 115 above gear 140. Gear 144 is positioned so as to be located in proximal portion 72 of drive head recess 74. A set screw, (not illustrated) disposed in threaded bore 149 presses against shaft flat 116 of drive shaft 114. The set screw holds the gear 144 to the drive shaft 114.

A gear 150, seen in FIG. 12, is fitted over the end of stem 98 of drive shaft 96. Gear 150 has a head 152 with teeth (not identified). In one version of saw 50 of this invention, gears 144 and 150 are designed so that there is a 2:1 ratio in the teeth on gear head 146 to the teeth on gear head 152. A neck 154 formed integrally with head 150 extends upwardly from the head of gear 150. A bore 156 extends axially through gear head 152 and neck 154. Bore 156 is dimensioned to receive drive shaft stem 98. A threaded bore 158 extends radially from the outer surface of gear neck 154 to bore 156 (threading not illustrated). Upon assembly of saw 50, gear 150 is positioned so as to be located in distal portion of 78 of drive head recess 74. Gear 150 is positioned so that the gear teeth engage the complementary teeth of gear 144. When the saw 50 is so assembled, it will be noted that gear necks 148 and 154 are adjacent the surface internal to the drive head 72 that defines the base of recess 72. A set screw (not illustrated) disposed in bore 158 presses against flat 102 integral with drive shaft 96. The set screw thus holds gear 150 to drive shaft 96.

A cover 160, seen only in FIG. 2, extends over the bottom of drive head 72. Cover 160 thus extends over drive head recess 74 as well as the components disposed in the recess. These components include the portion of the motor output shaft 132 that extends forward from neck 70 and bevel gears 134 and 140. Fasteners, (not illustrated) hold the cover 160 to the head.

Figure 14:
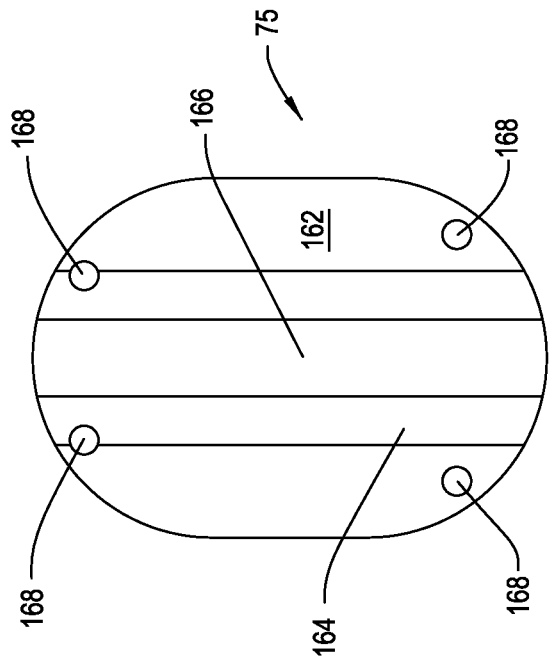
FIG. 14 is a plan view of the bottom of the cap of FIG. 13.
Figure 13:
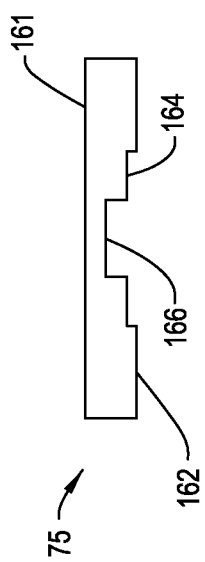
FIG. 13 is a plan view of the front of the cap disposed over the drive head.

Cap 75, seen in FIGS. 13 and 14, is formed from a single piece of metal. When viewed from the top, the cap 75 is generally oval in shape so as to fit over drive head top surface 73. Cap 75 is further formed to have a planar top surface 161. Opposite the top surface 161, the cap 75 has a bottom surface 162. Bottom surface 162 is the surface of the cap that abuts drive head top surface 73. The cap 75 is further formed to have two grooves 164 and 166 that extend inwardly relative to bottom surface 162. Both grooves 164 and 166 extend longitudinally along the whole of the length of the cap 75 and are centered on the longitudinal axis that extends along the cap. Groove 164 is the groove that extends inwardly directly from the bottom surface 162. Groove 166 extends inwardly from the base of groove 164. Thus, the base of groove 166 is, in comparison to the base of groove 164, closer to cap top surface 161. Both grooves 164 and 166, in the plane parallel to the plane of FIG. 13, are rectangular in cross section. Groove 164 has a depth approximately 0.1 mm greater than the thickness of blade 52. Groove 164 has a width across 5 mm greater than the pivotally sweep of the proximal end of the blade when actuated by drive pins 106 and 120. Groove 166 has a depth, the distance from cap bottom surface 162 to the base of the groove, that is 2 mm greater than the distance pins 94, 106, and 120 extend upwardly from drive head top surface 73.

Cap 75 is further formed to have four bores 168 that extend through the cap, from top surface 161 to bottom surface 162. Bores 168 are positioned so that when the cap 75 is placed over the drive head 74, each cap bore 168 is in registration with a separate one of the threaded cap bores 90. Threaded fasteners 170 that extend through bores 168 into drive head bores 90 removably hold the cap 75 to the drive head 74. When blade 52 is seated on the drive head top surface 73, and the cap 75 is secured over the drive head, the cap removably holds the blade to the drive head. As a consequence of the presence of groove 164, the blade 52, while restrained from vertical movement relative to the drive head 72, is able to engage in both translational movement and a pivoting movement. Groove 165 allows drive pins 106 and drive pins 120 to freely move even though cap 75 is seated over drive head top surface 73.

Sagittal saw blade 52 of this invention, as seen in FIG. 15, is a single piece of planar metal, typically sterilizable stainless steel. The blade 52 has opposed proximal and distal ends 176 and 184, respectively. Openings 178, 180 and 182 are formed in the blade so as to be located closer to proximal end 176 than distal end 184. Each opening 178, 180 and 182 is oval in shape. Opening 178, the distalmost of the openings, formed in the body of the blade 52 so that the major axis of the opening overlaps the longitudinal axis of the blade. Opening 180 is spaced proximally away from opening 178. The blade 52 is shaped so that major axis through opening 180 is perpendicular to the longitudinal axis of the blade. Opening 182 is the most proximal of the three openings and is spaced proximally away from opening 180. Opening 182, like opening 178, is oriented so that the major axis of the opening 182 overlies the longitudinal axis of the blade 52. The blade is also shaped so that each opening 178, 180, 182 allows the respective, pins, 94, 106 or 120 to freely move in the opening. Blade 52 is further formed so that teeth 186 extend forward from blade distal end 184.

Saw 50 of this invention is prepared for use by first removing cap 75 from the drive head 74 so that the blade 52 can be attached to the drive head. Blade 52 is seated over head top surface 73 so that: static pin 94 seats in blade opening 178; drive pin 106 seats in blade opening 180; and drive pin 120 seats in blade opening 182. Cap 75 is secured over drive head 74 so as to hold the blade to the drive head. At this stage, saw 50 is ready for use.

As seen in FIG. 15, the drive assembly drive shafts 96 and 114 are arranged so that when the blade 52 is in a center position, longitudinally aligned with the longitudinal axis of the drive head 74, drive pin 106 is in the leftmost position within opening 180 and drive pin 120 is in the topmost position within opening 182.

Saw 50 is actuated by depressing trigger 64. In response to the depression of the trigger 64, the control module causes energization signals to be applied to the motor 60. The activated motor rotates output shaft 132 and bevel gear 134. Bevel gears 134 and 140 cooperate to transfer the rotational power output by the motor to drive shaft 114. Gears 144 and 150 transfer the rotational power from drive shaft 114 to drive shaft 96. Drive shafts 96 and 114 are thus simultaneously rotated in opposed directions. Owing to the tooth ratio of gears 144 and 150, drive shaft 96 rotates at twice the speed at which shaft 114 rotates. Drive pins 106 and 120, rotate in the same directions and at the same speeds as the associated shafts, respectively, shafts 96 and 114.

The rotation of the drive pins 106 and 120 cause the displacement of the blade 52. More particularly, as a result of a single complete cycling of the blade 52 by saw drive pins 106 and 120, each tooth 186 of the blade moves in the loop pattern depicted in FIG. 16. As discussed below, a complete cycling of the blade 52 comprises a number of distinct phases of movement of the drive pins 106 and 120. In each phase of movement of the drive pins, drive pin 106 rotates 90°. Drive pin 120 rotates at only half the speed, half the frequency, of drive pin 106. Accordingly in each phase of the complete saw actuation cycle, drive pin 120 only rotates 45°.

Figure 16:
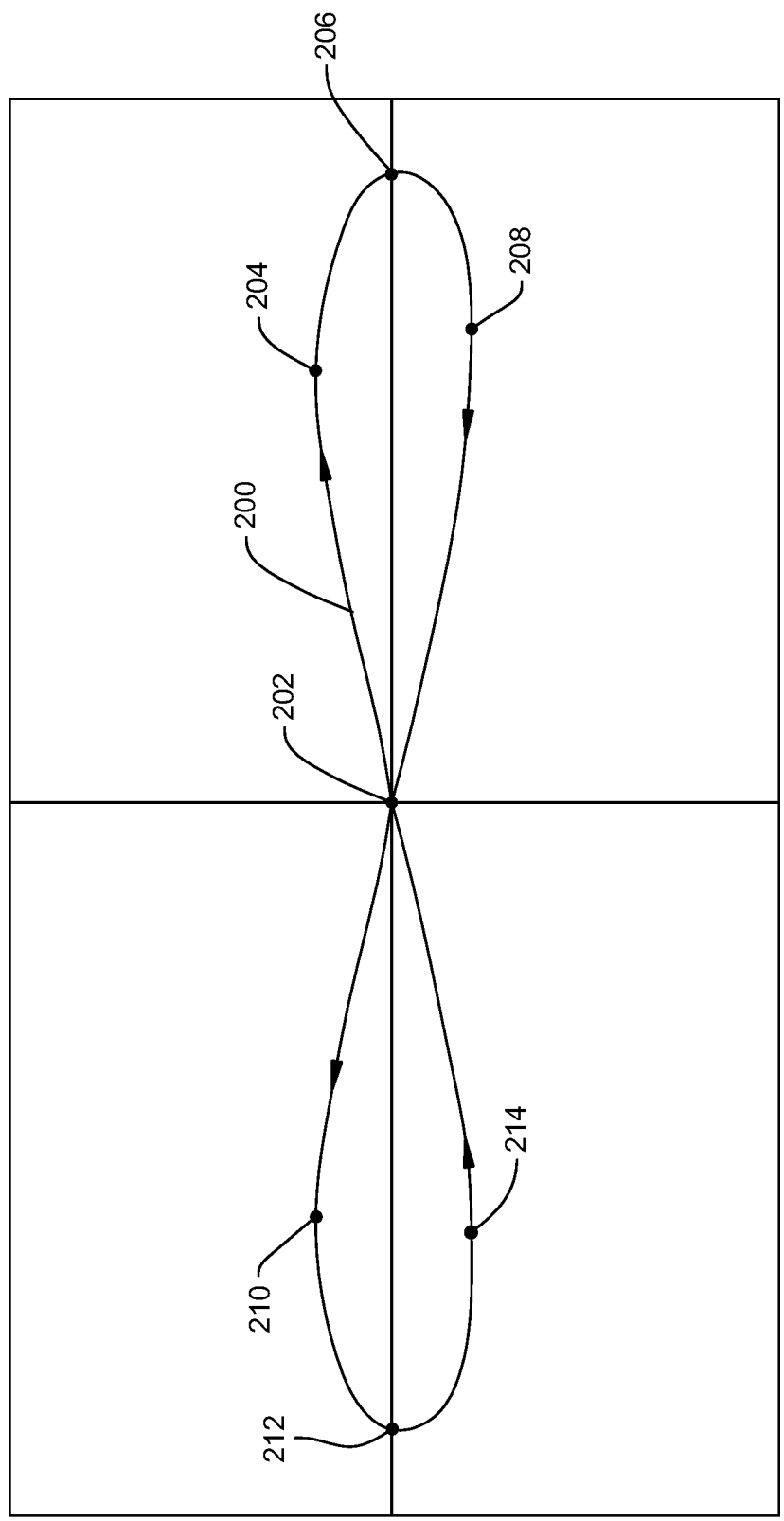
FIG. 16 depicts the path of travel loop of the tip of a tooth of blade that is actuated with the saw of this invention.

In the initial phase of the actuation of saw 50 and the resultant displacement of the blade 52 depicted in FIG. 16, drive pin 106 pushes forward on the surface of the blade that defines the distal end of opening 180. This displacement of drive pin 106 is represented by curved arrow 188 of FIG. 15. This pin-against blade abutment moves the whole blade 52 distally forward. This distal movement and below discussed complementary proximal movement, is along a line that represents an extension of the longitudinal axis of the blade. This axis is in the plane in which the blade is oriented. Simultaneously, pin 120 rotates counterclockwise as represented by curved arrow 189 of FIG. 15. The presence of static pin 94 in opening 178 constrains blade 52 to pivotal motion around the pin 94. Consequently, when blade proximal end 176 is displaced in one direction, to the right or left of the drive head longitudinal axis, the constraining effect of pin 94 causes the portion of the blade forward of pin 94 to pivot around the pin 94 in the opposed direction. Thus, in this initial phase of movement of the blade 52, the leftward displacement of the blade proximal end 176 results in the pivoting to the right of the blade distal end 184 and teeth 186. This pivoting around pin 94 is thus the pivoting around an axis that extends through the plane in which the blade is oriented.

In sum, in this initial phase of displacement of the blade 52 by saw drive pins 106 and 120, a single blade tooth is moved both distally forward and to the right. This is the movement along loop 200 between points 202 and 204 of FIG. 16. Point 202 it is understood is typically disposed along a longitudinal axis that extends between the opposed proximal and distal ends of the saw 50.

As a result of saw drive assembly undergoing this first phase of the displacement, drive pin 106 is in the center position in blade opening 180. Drive pin 120 is in a position between the distal end of blade opening 182 and the center of the opening 182.

The continued rotation of shaft 96 and attached pin 106 therefore pushes blade 52 rearwardly. Simultaneously, the rotation of shaft 114 and pin 120 continues to pivot blade distal end 184 and adjacent teeth 186 to the right. Thus, in this phase, of blade displacement the blade tooth moves along loop 200 from point 204 rearward and to the right to point 206.

The retraction of the blade teeth 186 away from the bone during this phase of blade displacement allows bone remnants that have accumulated during any early phase of the teeth displacement cycle to move away from the face of the bone being cut. More specifically, what occurs during this retraction of the blade is that bone chips and bone dust that adhering to the teeth are pulled away from the bone. Consequently, during the retraction of the teeth away from the bone, these remnants break free of the blade. During subsequent sweeps of the blade 52, these remnants are then pushed rearwardly, further away from the face of the bone being cut.

At the start of the next phase of the actuation of the blade 52, drive pin 106 is in the rightmost position in opening 180. Drive pin 120 is in the center of blade opening 182. During this phase of saw actuation, the continued rotation of drive shaft 94 results in the continued rearward displacement of the blade teeth 186. Specifically, the displacement causes the tracked blade tooth 186 to move rearward of loop center point 202. Also at the start of this phase of blade actuation, drive pin 120 will have rotated 90° from its initial position. Drive pin 120 will therefore be in the center of blade opening 182. The continued actuation of drive shaft 114 results in drive pin 120 starting to push blade proximal end 176 to the right. This displacement of the blade 52, results in the blade distal end 184 and teeth 186 moving to the left. The collective effect of drive pins 106 and 120 on the blade is to cause the blade tooth to move along the loop between points 206 and 208.

At the time the blade tooth reaches point 208 on loop 200, drive pin 106 is back in the center of blade opening 180. Drive pin 120 is between the center of opening 182 and the proximal end of opening 182.

With the start of the next phase of the actuation of the saw 50 drive assembly, drive pin 106 starts to push the blade 52 forward. Drive pin 120 continues to pivot the blade distal end 184 and teeth 186 to the left. During this phase of saw actuation, the blade is thus moved both forwardly and to the right. More particularly as a result of this phase of the operation of the saw 50 the tracked blade tooth 186 will have moved along loop 200 from point 208 back to centerpoint 202.

At this time the saw drive assembly will have engaged in one-half of a complete actuation cycle. Drive shaft 96 and drive pin 106 will have rotated a full circle, 360°. Drive pin 106 will be back where it is depicted in FIG. 15, in its leftmost position within blade opening 180. Drive shaft 114 and drive pin 120 will only have rotated 180°. Drive pin 120 will therefore be in the proximalmost position within blade opening 182.

The next four phases of operation of the saw drive shafts 96 and 114 are symmetric to the first phases. It should be understood that center point 202 is the point of symmetry of loop 200. The tracked tooth in the next phase, the fifth phase of the cycle, moves distally and to the left, from center point 202 to point 210. In the sixth phase of the cycle, the tooth continues to move to the left. In this cycle drive pin 106 starts the tooth into a rearward, proximal displacement. Accordingly, the tooth will move from point 210 to point 212.

At the start of the seventh phase, the rotation of the drive pin 120 starts the tooth on a rightward pivotal displacement. Drive pin 106 continues to urge the tooth proximally. The tooth therefore moves along loop 200 from point 212 to point 214. In the eighth and final phase of the cycle, the rotation of drive pin 106 restarts the tooth on a forward displacement phase. Drive pin 120 continues to cause the tooth to pivot to the right. The tooth will therefore move along the loop from point 214 back to center point 202. The return of the tooth 186 to center point 202 is the completion of the tooth traveling through a full displacement cycle.

It should therefore be understood that, during a single complete cycle of the actuation of the blade 52, drive pin 106 will have rotated 720° while drive pin 120 will have rotated 360°. The drive pins therefore displace the blade as depicted in the loop of FIG. 16 where one segment of the travel of a blade tooth of the blade crosses over a previous segment of the travel of the tooth.

II. Second Embodiment

Figure 17:
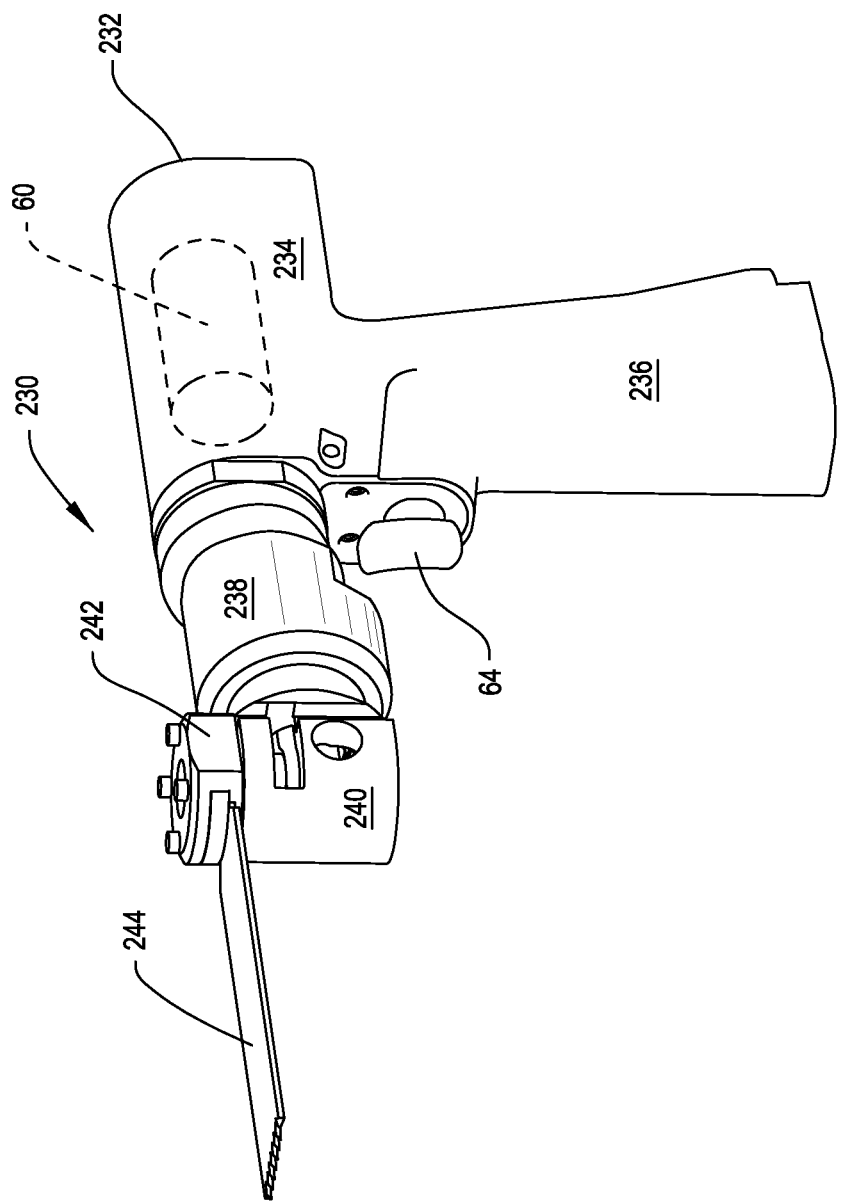
FIG. 17 is a perspective view of an alternative surgical sagittal saw of this invention.

An alternative surgical sagittal saw 230 is now described by initial reference to FIG. 17. Saw 230 includes a body 232 similar to first described saw body 54. Body 232 has a barrel shaped base 234 analogues to body head 56 of saw 50. A grip 236 extends downwardly from base 234. A motor 60 is disposed in body base 234. Not shown is a battery that is attached to the butt end of the grip 236 that provides power for actuating the motor 60. A neck 238 extends forward from body 232. A head 240 is mounted to the distal end, the free end of neck 238. A blade mount 242 is mounted to head 240. The blade mount 242 is mounted to the head so as to be able to oscillate around an axis that extends through the head. Blade mount 242 includes components that releasably hold a sagittal saw blade 244 to the mount.

Blade mount 242 is part of the drive assembly of saw 230. Also part of the drive assembly are a drive link 246 (FIG. 31) and a toggle link 248 (FIG. 37) Both the drive link 246 and the toggle link 248 are connected to motor 60 and extend through neck 238 to head 240. The toggle link 248 has a head 462 that engages saw blade 244. Upon actuation of the motor 60, the drive link 246 pivots blade mount 242 back and forth. This pivoting of the blade mount causes the blade 244 to oscillate back and forth, to the left and right of the longitudinal axis that extends through saw base 234, neck 238 and head 240. Simultaneously, the toggle link 248 is reciprocated so as to cause the link head to engage in repetitive forward/back/forward/back motion. This reciprocation of the toggle link 248 causes the blade to, simultaneously while being oscillated to the right and left, to be reciprocated between distal (forward) and proximal (rearward) positions.

Figure 23:
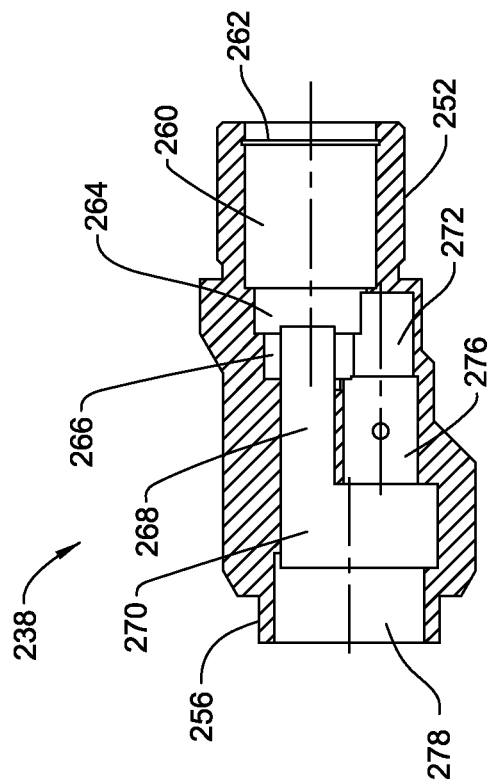
FIG. 23 is a cross sectional view of the saw neck taken along line 23-23 of FIG. 22.
Figure 22:
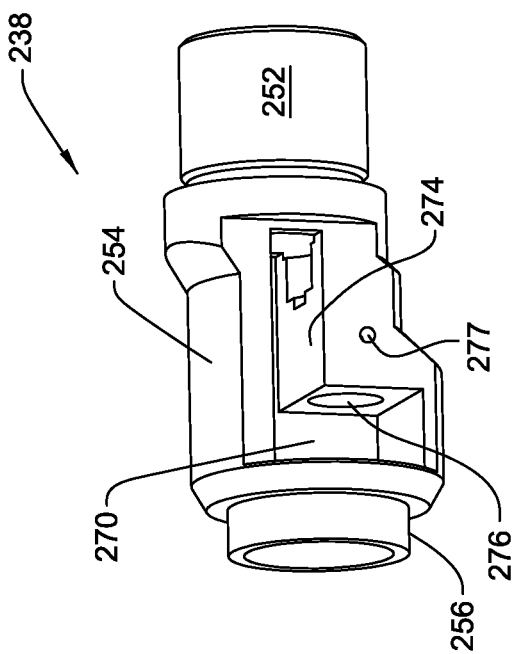
FIG. 22 is a side plan view of the saw neck, with the outer wall removed.

Neck 238, now described with respect to FIGS. 22 and 23, is formed from a single piece of metal. A cylindrical proximal end sleeve 252 forms the most proximal portion of neck 238. The outer surface of sleeve 252 is provided with threading, (not illustrated.) When saw 50 is assembled, neck sleeve 252 is seated in a complementary opening in the proximal end of saw body base 234. The sleeve threading engages complementary threading around the interior surface of base 234 so as to hold neck 238 to saw body 232.

Forward of proximal end sleeve 252, neck 238 has a shell 254. In FIGS. 22 and 23, the shell is shown open. This is to show the features of the neck internal to the shell 254. In the working version of the saw 230, the shell 254 is closed. In cross section, the outer surface of frame is circular. In terms of relative dimensions, the outer surface of shell 254 extends radially beyond the outer surface of sleeve 252. The relatively large outer diameter of neck shell 254 limits the extent the neck can be threadedly secured into the saw base 234. Neck 238 is designed so that the shell 254 is not of constant diameter or coaxial with sleeve 252. Instead, neck 238 is shaped so that shell 254 has a number of sections that, extending forwardly from sleeve 252, step downwardly from the sleeve, (individual sections not identified).

A distal end sleeve 256 extends forward from shell 254 and forms the most distal portion of neck 238. Sleeve 256 has a cylindrical outer wall. Neck 256 is further shaped so that distal end sleeve 256 is centered on a longitudinal axis that is parallel to and axially offset from proximal end sleeve 252. Distal end sleeve 256 is shorter in length than proximal end sleeve 252.

Neck 238 is formed so as to define a number of void spaces internal to the neck. One of these voice spaces is bore 260. Bore 260 extends distally forward from the free end of proximal end sleeve 252. Bore 260 extends essentially the whole of the length of the proximal end sleeve 252. An annular groove 262 extends inwardly from the cylindrical wall internal to sleeve 252. Groove 262 extends circumferentially around bore 260 and is located a short distance distally forward of the open proximal end of bore 260.

A number of void spaces are within neck shell 254. One of these void spaces is space 264. This is the space in the proximal end of shell 254, the space into which bore 260 opens. Void space 264 opens up into a void space 266. Void spaces 264 and 266 are both circular in cross section and concentric with bore 260. Void space 264 has a smaller diameter than bore 260. Void space 266 has a smaller diameter than void space 264. A void space 268 extends forward of void space 266. Void space 268 opens up into a void space 270. Void space 270 subtends a greater cross sectional area than void space 268. Void spaces 268 and 270 are not concentric. In FIG. 23, void space 270 is shown as having a upper portion into which void space 268 opens and a contiguous lower portion (portions of void space 270 not identified). The lower portion of void space 270 is spaced laterally away from void space 268. Void space 270 is the most distally located of the void spaces in neck shell 254.

Neck shell 254 is further formed to have two additional void spaces. One of these void spaces, void space 272 is located below and is contiguous with void spaces 264 and 266. Void space 272 thus subtends an area that is offset and below the area subtended by bore 260. The distal end of void space 272 opens into a void space 276. Void space 276 is located below void space 268. A web 274 internal to neck shell 254 separates void space 276 from void space 268. Void space 276 is circular in cross sectional shape. The distal end of void space 276 opens into the portion of void space 270 below void space 268. A through bore 277 intersects void space 276. Bore 277 extends through the void space 276 along an axis that intersects with and is perpendicular to the longitudinal axis through void space 276. Saw neck 238 is formed so that bore 277 extends along a plane located approximately in longitudinal mid-section of void space 276. Bore 277 is formed with threading, (not illustrated).

A bore 278 extends distally forward of void space 270. Bore 278 is disposed in neck distal end sleeve 256. Bore 278 forms the open distal end of neck 238. The neck 238 is formed so that threading not identified extends around the cylindrical wall internal to distal end sleeve 256 that defines bore 278.

Figure 24:
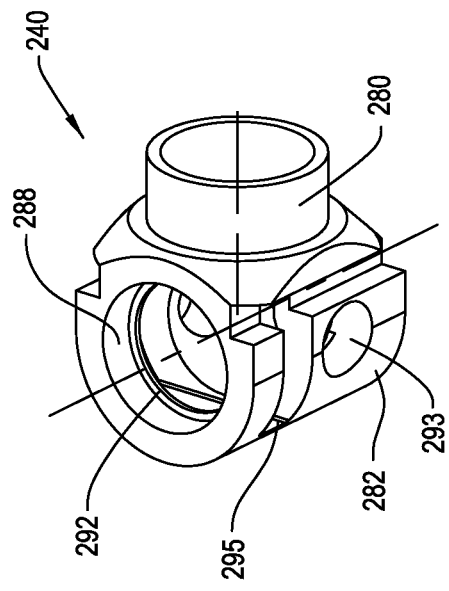
FIG. 24 is a perspective view of the head of the surgical sagittal saw of FIG. 17.
Figure 25:
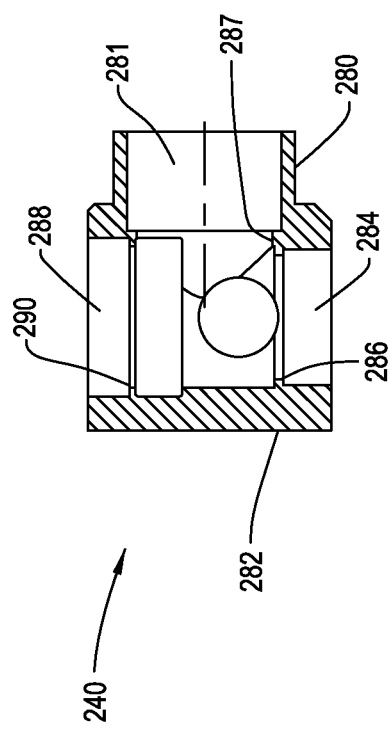
FIG. 25 is a cross sectional view through the saw head of FIG. 24.

The saw head 240, now described by reference to FIGS. 24 and 25, is formed from a single piece of metal. Saw head include a cylindrical sleeve 280. Sleeve 280 is dimensioned to seat in the neck bore 278. The outer surface of sleeve 280 is provided with threading, (not identified). The threading of head sleeve 280 engages the threading of neck sleeve 256 so as to facilitate the screw securement of head 240 to neck 238. A bore 281 extends distally forward from the proximal end of sleeve.

Forward of sleeve 280, head 240 includes a frame 282 that forms the exposed body of the head. The head 240 is shaped so that frame 282 extends radially outwardly beyond the distal end of sleeve 280. In FIG. 25, the longitudinal axis of sleeve 280 is shown as extending horizontally; the longitudinal axis through frame 282 extends vertically. Saw head 240 has an outer face that, in planes perpendicular to the longitudinal axis through the frame 282, appear U-shaped. Specifically, from the most distal location along the face of head frame 282 the head curves both outwardly and proximally.

A number of contiguous bores collectively form a top-to-bottom through opening through saw head frame 282. In FIG. 25 a bore 284 is seen extending upwardly from the bottom of the frame. Bore 284 extends upwardly from the portion of the frame 282 located below sleeve 280. Saw head 240 is further formed so that a circular lip 286 extends inwardly from the cylindrical internal wall of frame 282 that defines bore 284. Lip 286 is located slightly above where sleeve 280 extends proximally from frame 282. Sleeve bore 281 opens into frame bore 284. Internal to the frame 282 a circular lip 287 extends inwardly immediately forward of the distal end of sleeve bore 281. Not identified is the circular void space defined by lip 287 that is the transition space between sleeve bore 281 and frame bore 284.

Saw head 240 is further formed to define a bore 288 internal to frame 282 that is located above and contiguous with frame bore 284. Bore 288 has a diameter that is greater than that of frame bore 284. Bore 288 opens into the top of frame 282, which is the top of saw head 240. Frame 282 is further shaped so as to have a circular lip 290 that extends into bore 288. Lip 290 extends inwardly from the internal cylindrical wall of saw head 240 that defines bore 288. In the illustrated version of the invention, webbing internal to frame 282 that defines a portion of lip 286 also defines a portion of lip 290.

In the illustrated version of head 240, an opening 293 extends laterally through head frame 282. Opening 293 extend through the opposed sides of the frame and is oriented along an axis perpendicular to the longitudinal axis that extends through bores 284 and 288. Opening 293 intersects both bore 284 and a section of lip 286. An opening 295 extends side-to-side through frame 282. Opening 295 intersects bore 288 below lip 290. Openings 293 and 295 are present for manufacturing purposes and may not be present in many versions of the invention.

The blade mount 242, now described in detail by reference to FIGS. 26-28, is also formed from a single piece of metal. Blade mount has a stem 298 the outer surface of which is arcuate. The blade mount 242 is however formed so that the stem 298 is not completely cylindrical. Stem 298 has a notch 302 that extends forward from the proximally directed side of the stem. The notch 302 extends upwardly from the base of the stem 302. Stem 298 is further formed so that, at the proximally facing portion of the stem, notch 302 is bordered on three sides by a frame 304. Frame 304 has a planar outer surface. Stem 298 is further formed to have a pair of opposed flat faces 306. One face 306 is directed distally forward; the opposed face is directed proximally rearwardly. The proximally directed face 306 is located immediately above frame 304. Faces 306 are symmetrically opposed to each other relative to the longitudinal axis through blade mount stem 298. Blade mount stem 298 is further formed so as to have groove 307 that extends inwardly from the outer face of the stem. Groove 307 is located immediately above the bottom end, the base end, of the stem 298. The groove 307 extends arcuately around the outer face of the stem 298 in a plan perpendicular to the bottom-to-top longitudinal axis through the stem.

The blade mount stem 298 is further formed to have a window 308 that extends inwardly from the distally directed face of the stem. Window 308 is both located above the base of stem 298 and opens into notch 302. The stem 298 is further formed to have a bore 310. Bore 310 extends sides to side through the frame so as to be on an axis that is perpendicular to the longitudinal axis running through the stem 298. The bore 310 is located above the bottom end of the frame. Specifically, bore 310 intersects a portion of notch 302 into which window 308 opens.

Above stem 298, blade mount 242 is formed to have first and second necks 312 and 316, respectively. Both necks 312 and 316 are coaxial with stem 298. First neck 312 is the portion of the blade mount 242 contiguous with stem 298. First neck 312 is generally cylindrical in shape and has a radius greater than the radius of curvature of stem 298. While the first neck 312 is generally cylindrical, the neck is formed so as to have on the outer surface two parallel opposed flats 314. One flat 314 is distally directed. The opposed flat 314 is proximally directed. Flats 314 are present to facilitate the removal of the drive link 246 from the blade mount 242.

Blade mount second neck 316 is located immediately above first neck 312. Second neck 316 has a diameter greater than that of first neck 312. The second neck 316 is shorter in length than the first neck 312.

The blade mount 242 has a head 318 disposed above and integral with the second neck 316. The blade mount 242 is shaped so head 318 extends radially beyond the second neck 316 around the whole of the circumference of the second neck. In the illustrated version of the invention, blade mount head 318 is shaped to have opposed front and rear faces and side faces (individual faces not identified). The head front face is convex in shape such that rearward of the distal most section of the face on the opposed curved back both rearwardly and outwardly. The head rear face is symmetric with the front face. Forward of the distal most section of the rear face, on the opposed sides of the face, the face curves forwardly and outwardly. The opposed side faces each extend between the front and rear faces. The side faces are planar and parallel to each other.

A slot 320 extends longitudinally through blade mount head 318 from the front face to the rear face. The front face and rear face openings into the slot 320 are rectangular in cross section. The blade mount 318 is further formed so that within the head 318 steps 322 extend into the opposed sides of slot 320. Each step 322 extends inwardly from the wall internal to the head 318 that defines one of the sides of slot 320. The steps 322 extend over the internal horizontal surface of the slot (when viewed in FIG. 27) that defines the base of the slot 320. Thus the width across slot 320 where steps 322 are present is less than the width across the slot above the steps. For reasons that will be apparent in the description of the operation of the invention, the steps 322 have a height, extend above the base of slot 320, a distance that is approximately 0.05 mm greater than the thickness of the blade 244 inserted in the slot. The forwardly directed distal face of each step 322 is recessed proximally rearward from the adjacent head front face. The rearwardly directed proximal face of each step 322 is recessed distally forward from the adjacent head rear face. Thus, immediately forward and rearward of steps 322, the width of the bottom section of slot 320 is equal to the width across the contiguous top section of the slot.

A number of bores extend longitudinally, bottom to top, through the blade mount 242. A first bore, bore 324 in FIG. 28 extends upwardly from the bottom of stem 298 through the stem. Bore 324 thus intersects stem notch 302 and stem bore 310. The blade mount 242 is shaped so that the diameter of bore 324 is greater than the width across notch 302. Bore 324 extends a short distance into the first neck 312 of the blade mount 242. A second bore, bore 326 extends upwardly from bore 324. Bore 326 is coaxial with and has a diameter greater than bore 324. Bore 326 extends partially but not completely through blade mount first neck 312. A third bore, bore 328, extends upwardly from bore 326. Bore 328 is coaxial with and has a diameter greater than bore 326. Bore 328 extends upwardly through the top of the blade mount first neck 312, the second neck 316, and the blade mount head 318. Bore 328 has an open end in the top of the blade mount head 318. Bore 328 also intersects head slot 320.

The blade mount head 318 is further formed to have four additional threaded bores 330 that extending downwardly from top surface of the plate, (threading not shown). Bores 330 are located forward of, rearward of and to the sides of the opening into bore 328. Bores 330 open into slot 320.

Figure 19:
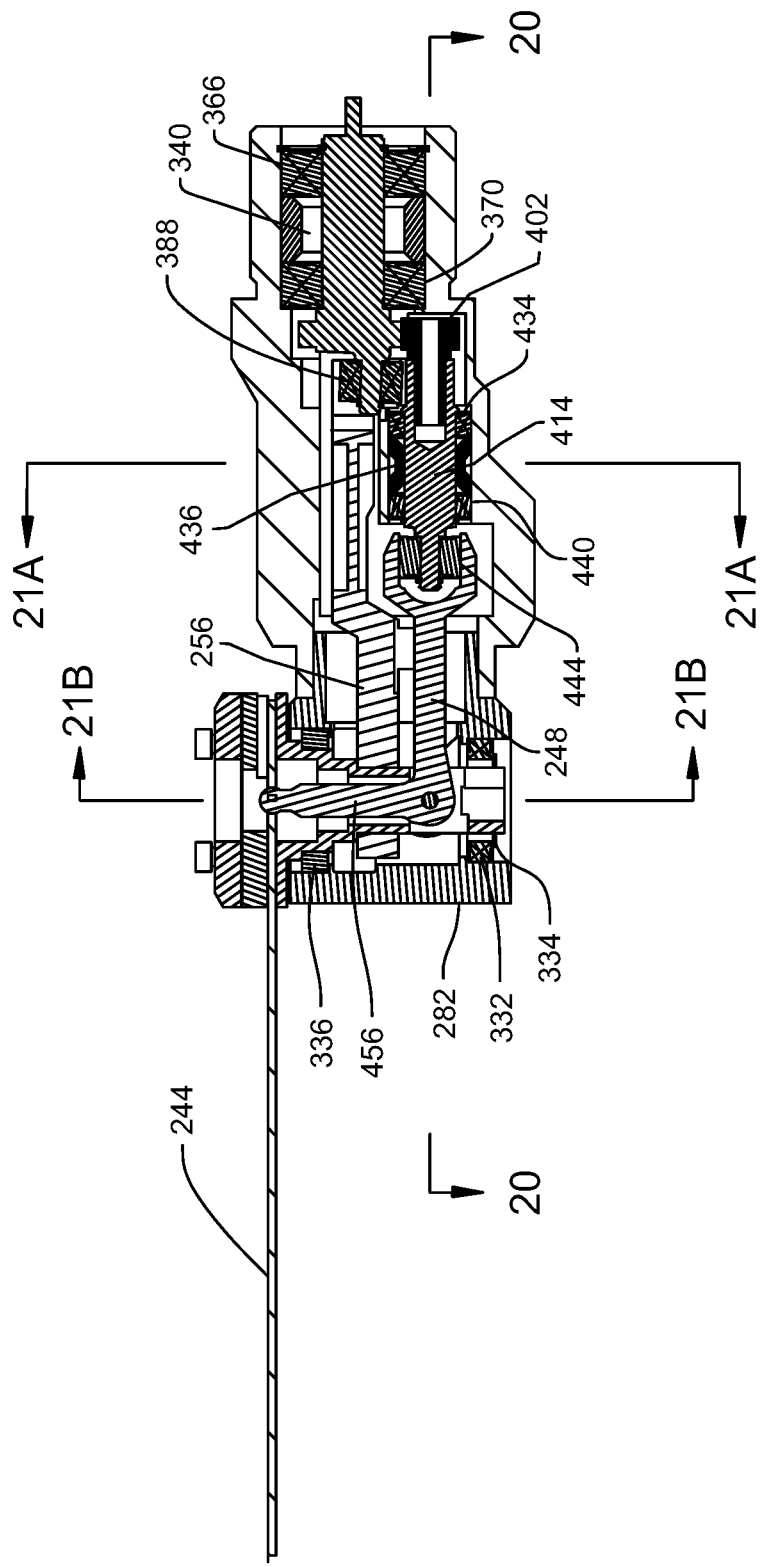
FIG. 19 is a cross sectional view of the saw of FIG. 17 taken in a vertical plane through which the longitudinal axis of the neck extends.
Figure 21B:
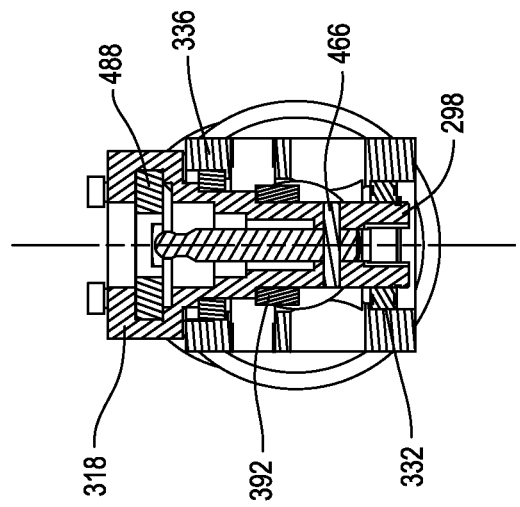
FIG. 21B is a cross sectional view of the saw head and blade mount taken along line 21B-21B of FIG. 19.

From FIGS. 19 and 21B it can be seen that the blade mount 242 is rotatably held in head frame 282 by two bearing assemblies 332 and 336. While not specifically illustrated, it should be understood that each bearing assembly 332 and 338 has an inner and outer race. Specifically, the blade mount is positioned so that the mount stem 298 and the bottom of the first neck 312 are disposed in saw head bore 284. The upper section of the first neck 312 and substantially all of the second neck 316 are disposed in saw head bore 288. A first bearing assembly, bearing assembly 332, extends between blade mount stem 298 and the adjacent inner wall of the saw head that defines bore 284. The inner race of bearing assembly 332 is pressed against the section of blade mount stem 298 located below window 308. A snap ring 334 is seated in stem groove 307. When saw 230 is assembled the downwardly directed of the inner race of bearing assembly 332 seats against the portion of the snap ring 334 that extends radially beyond the blade mount stem 298. Snap ring 334 thus holds bearing assembly 332 in saw head bore 284. Also, upon assembly of saw 50, the outer race of bearing assembly 332 seats against the downwardly directed annular face of lip 286. The abutment of the bearing assembly outer race against lip 286 prevents upward movement of the bearing assembly 332.

The second bearing assembly, bearing assembly 336, has an inner race disposed around the circular section of blade mount first neck 312 above flats 314. The outer race of the bearing assembly 336 is seated against the cylindrical wall of the saw head 240 that defines the portion of bore 288 above lip 290. More particularly, the outer race of bearing assembly 336 is disposed against saw head lip 290. The inner race of bearing assembly 336 is seated in the circular step present where the blade mount second neck 316 extends radially outwardly from the first neck 312. It should be understand that, collectively the components forming saw 50 are constructed so that when the saw is assembled, there is separation between the top of the saw head 240 and the adjacent and overlying undersurface of blade mount head 318. This separation and low friction interface provided by bearing assemblies 332 and 336 ensure that the blade mount 242 is able to freely rotate within the saw head 240.

The power to actuate saw blade 244 comes from an output shaft similar to output shaft 132 (FIG. 3) connected to motor 60. The rotational moment produced by the output shaft 340 is applied to a first drive shaft 340 now described by initial reference to FIGS. 29 and 30. Drive shaft 340 is formed from a single piece of metal and is shaped to have cylindrically shaped torso 344. Extending distally from torso 344, drive shaft 340 has a foot 342. Foot 342 is generally in the form of a rectangular panel. Foot 342 extends diametrically across the distal end of torso 342. The foot 342 is dimensioned to seat in a complementary slot formed in the proximal end of the motor output shaft to which drive shaft 340 is coupled. Immediately forward of the distal end of torso 344, the drive shaft 340 is formed to have a groove 346. Groove 346 extends circumferentially around and inwardly from the outer cylindrical surface of torso 344.

First drive shaft 340 is further shaped to have a neck 348 located immediately forward of torso 344. Neck 348 is cylindrical in shape. The neck 348 is coaxial with the torso 344 and has a diameter greater than that of the torso. Not identified is an undercut in the torso immediately proximal to neck 348.

A head 350 is located immediately forward of neck 348. Head 350 is cylindrical in shape. The first drive shaft 340 is shaped so that the head 350 is coaxial with the neck 348 and has diameter greater than that of neck 348. First drive shaft 340 is further shaped so that teeth 352 extend radially outwardly and circumferentially around head 350.

A cylindrical nose 356 extends distally forward of first drive shaft head 348. The nose 356, which has a diameter less than that of shaft torso 344. Nose 356 nose extends forward from a boss 354 which is immediately contiguous with the head 350. The boss 354 is circular in cross section and coaxial with the head 350. Drive shaft 340 is further formed so that boss 354 has distally directed front face, not identified, that is in plane not perpendicular to the common longitudinal axis of shaft torso 344, neck 348 and head 350. The shaft nose 356 extends forward from the front face of the boss head from a location off center with the head longitudinal axis. Shaft nose 356 thus has a longitudinal axis that is both off axis to and not parallel with the longitudinal axis through shaft torso 344, neck 348 and head 350. Immediately proximal to the distal end of nose 356 the nose is formed to have a groove 358, seen only in FIG. 30. Groove 358 extends circumferentially around and inwardly from the outer cylindrical surface of nose 356. Upon assembly of saw 50 for reasons that are apparent below, a snap ring 359, seen only in FIG. 29, is disposed over groove 358. Snap ring 359 extends radially beyond the outer surface of shaft nose 356.

Figure 20:
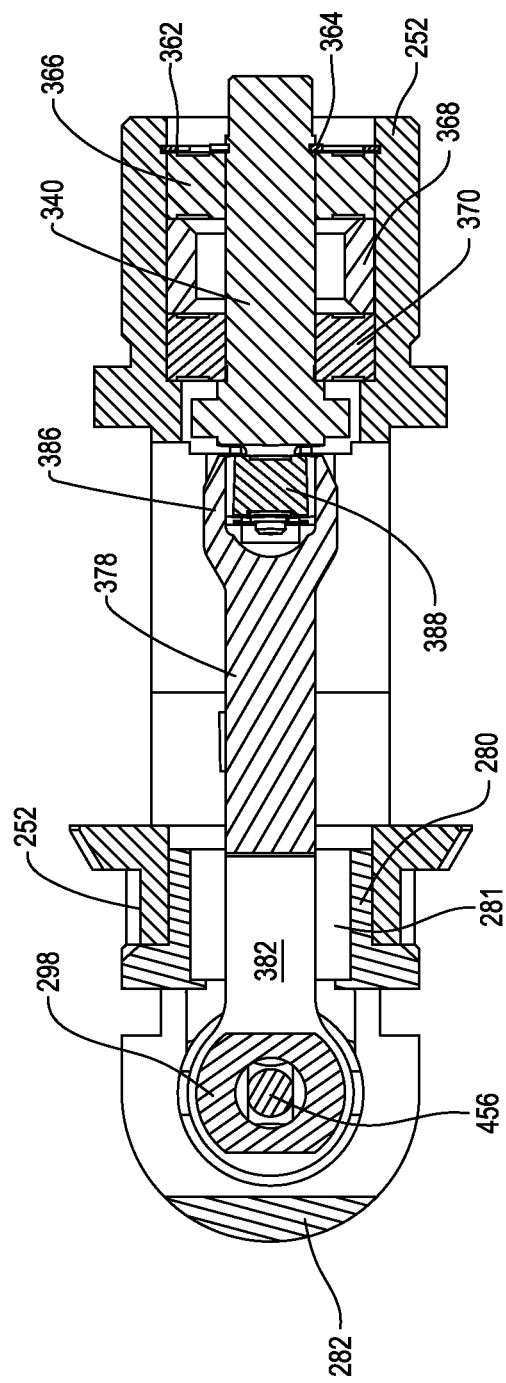
FIG. 20 is a cross sectional view of the saw neck and head of FIG. 19 taken along line 20-20 of FIG. 19.

From FIGS. 19 and 20 it can be seen that the first drive shaft 340 is rotatably mounted in neck bore 260. Two bearing assemblies 366 and 370 rotatably hold the shaft torso 344 in bore 260. Not specifically illustrated are the inner and outer races of bearing assemblies 366 and 370. The proximal most bearing assembly, bearing assembly 366, is positioned so as to be located immediately forward of neck groove 262 and shaft groove 346. A snap ring 362 is disposed in neck groove 262. A snap ring 364 is disposed in shaft groove 346. When saw 50 is assembled, the outer race of bearing assembly 366 seats against the portion of snap ring 362 that extends into bore 260. The inner race of bearing assembly 366 abuts the portion of snap ring 364 that extends radially beyond shaft torso 344. Snap rings 362 and 364 thus retain the bearing assembly 366 in the proximal end sleeve 252 of saw neck 238.

The second bearing assembly, bearing assembly 370, is positioned over the distal end of shaft torso 344. More particularly, bearing assembly 370 is arranged so that the distal end of the inner race of the assembly abuts the surface of the circular, rearward face surface of the shaft neck 348 immediately adjacent the distal end of the shaft torso 344. A spacer 368 is disposed against neck bore 260 between bearing assemblies 366 and 370. The outer surface of the spacer 368 is disposed against the cylindrical wall internal to the proximal end sleeve 252. The opposed ends of spacer 368 abut the facing outer races of bearing assemblies 366 and 370. Spacer 368 is spaced radially away from the portion of drive shaft torso 344 disposed between the bearing assemblies 366 and 370. Spacer 368 thus holds the bearing assemblies 366 and 370 apart from each other.

When drive shaft torso 344 is rotatably mounted in neck bore 266, the shaft foot 342 extends proximally a short distance beyond neck 238. Drive shaft neck 348 and head 350 are disposed neck void space 264. Shaft nose 356 is disposed in void space 266.

Figure 31:
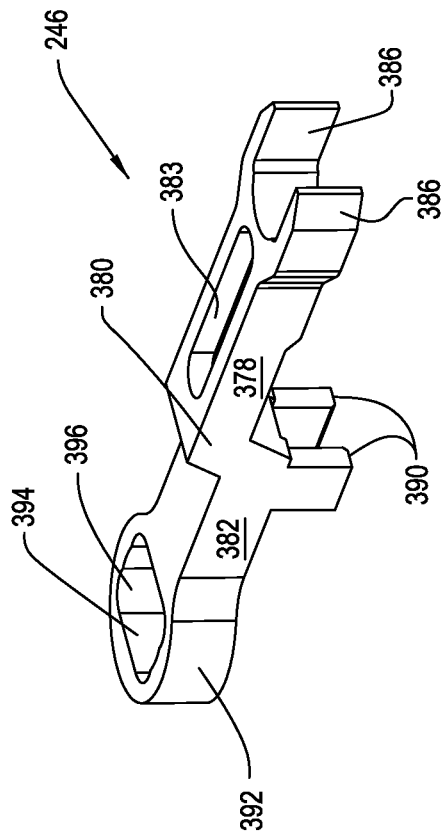
FIG. 31 is a perspective view of the drive link of the surgical sagittal saw of FIG. 17.
Figure 32:
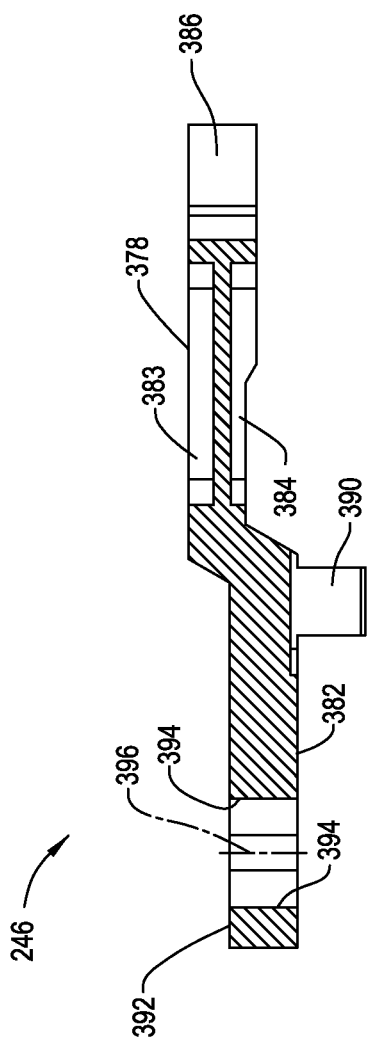
FIG. 32 is cross sectional view of the drive link of FIG. 31.

FIGS. 31 and 32 illustrate the structure of drive link 246 of saw 230. Drive link 246 is formed from a single piece of metal. The drive link 246 is shaped to have proximal and distal beams 378 and 382, respectively. Beams 378 and 382 are both rectangular in cross sectional shape. The beams are centered on longitudinal axes that are parallel though offset from each other. In the Figures, proximal beam 378 is shown disposed above distal beam 382. A web 380 extends diagonally between the beams 378 and 382 to connect the beams together. In the illustrated version of the invention, web 380 extends diagonally downwardly and distally away from the proximal end of proximal beam 378 to distal beam 382. Also in the illustrated version of the invention grooves 383 and 384 extend inwardly from the opposed top and bottom faces of proximal beam 378. Grooves 383 and 384 are present to reduce the overall mass of the drive link 246.

Drive link 246 is further formed to have two feet 386 that extend rearwardly from the proximal end of proximal beam 378. Feet 386 are spaced apart from each other and are symmetrically located relative to the longitudinal center axis of the proximal beam 378. Feet 386 are shaped apart a sufficient distance to receive therebetween a bearing assembly 388 disposed over drive shaft nose 356 (FIG. 20). Bearing assembly 388 has an outer race (not illustrated) with a geometry similar to that of a slice section of a sphere. The inner opposed faces of feet 386 may have surfaces with a slight concave curvature appropriate to facilitate the capture of outer race of bearing assembly 388 between the feet.

Two tabs 390 extend downwardly from the drive link distal beam 382. Tabs 390 extend down from beam 382 at the location immediately forward of where web 380 and the 382 meet. The outer side face of each tab 390 is flush with the adjacent outer side of the beam 382 from which the tab extends.

The drive link 246 is further formed to have a head 392 that is extends forward from distal beam 382. When viewed from the top down, the drive link head has an outer surface that appears circular in shape. An opening 396 extends top to bottom through head 392. The drive link 246 is formed so that opening 396 is dimensioned to receive the first neck 312 of blade mount 242. More particularly, the drive link is formed so that opening 396 is partially defined by two walls 394 internal to head 392. Walls 394 are parallel to each other and located on planes that are perpendicular to the longitudinal axis that extend through link distal end beam 382. The drive link 382 is formed so that walls 394 are spaced apart from each other so that, when saw 230 is assembled, the flat faces 306 integral with the blade mount 240 fit tightly between the walls 396.

As seen in FIGS. 19 and 20, upon assembly of the saw 50, the drive link 246 is arranged so that the proximal beam 378 is located in void spaces 268 and 270 internal to saw neck 238. Link feet 386 extend into void space 266. The feet are disposed around the opposed sides of bearing assembly 388. Bearing assembly 388 is disposed over shaft nose 356. It should be appreciated that the snap ring 359 (FIG. 29) disposed in nose groove 358 holds the bearing assembly 388 to drive shaft 340.

The link web 380 extends from neck void space 270 into neck bore 280. Distal beam 382 extends from neck bore 280 into bore 281 internal to the saw head 240. Drive link head 392 is disposed in the upper portion of saw head bore 284 and the lower portion of bore 288.

Figure 33:
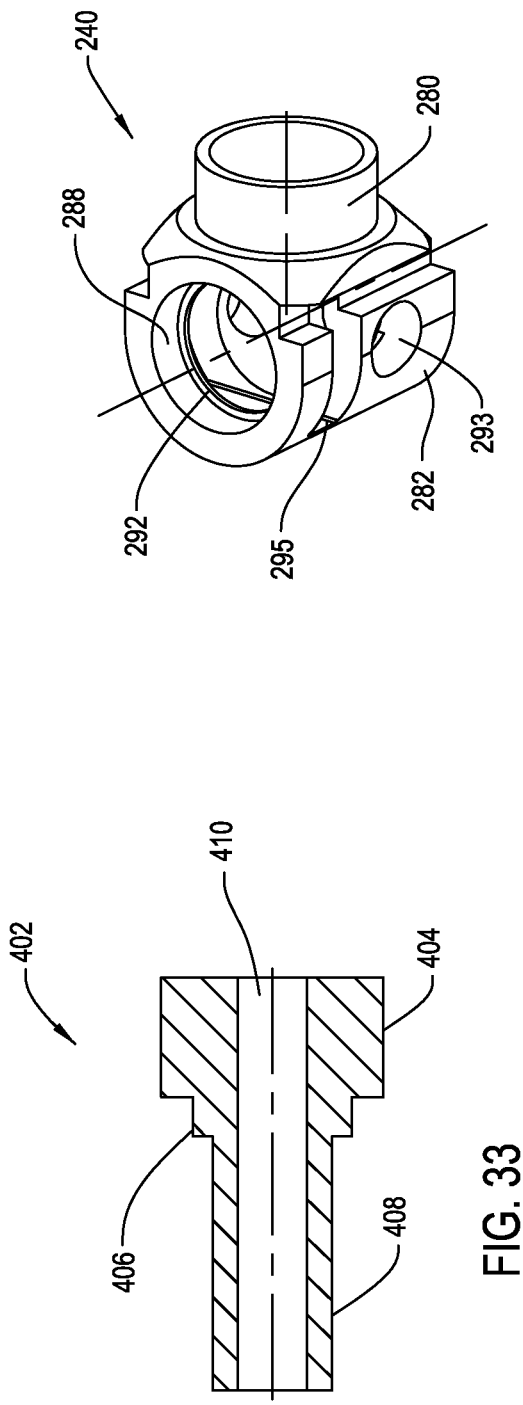
FIG. 33 is a cross sectional view of a transmission gear of the surgical sagittal saw of FIG. 17.

Also moveably disposed in saw neck 238 is a gear 402 and a second drive shaft 414. Gear 402, seen in cross section in FIG. 33, has a cylindrical head 404. Head 404 is formed to have teeth (not identified). The teeth integral with drive shaft head 404 are shaped to engage the teeth 352 of the first drive shaft. In one version of the invention, the ratio of teeth on the first drive shaft 340, to the teeth on the second drive shaft is 2:1.

Extending distally from head 404, gear 402 is formed to have a neck 406. Neck 406 is smaller in diameter than the gear head. A cylindrical stem 408 extends distally from neck 406. Stem 408 is smaller in diameter than neck 406. In terms of axially length, the stem 408 has a length greater than the combined length of the gear head 404 and neck 406. The gear 402 is formed so a bore 410 extends axially through the gear. Bore 410 thus extends through head 404, neck 406 and stem 408.

Figure 34:
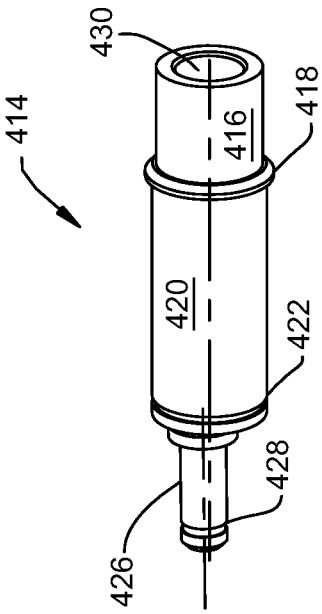
FIG. 34 is perspective view of the second drive shaft of the surgical sagittal saw of FIG. 17.
Figure 35:
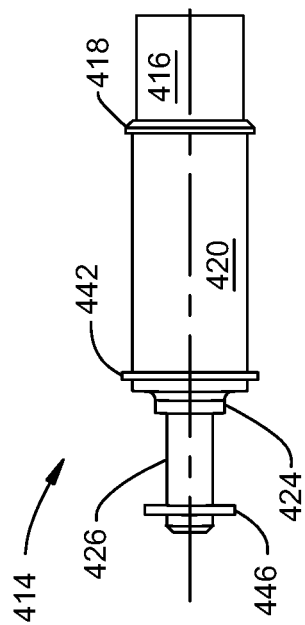
FIG. 35 is perspective view of the dive shaft of the surgical sagittal saw of FIG. 34.
Figure 36:
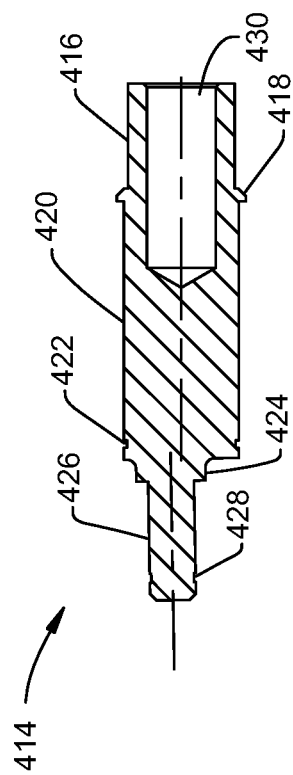
FIG. 36 is a cross sectional view of the second drive shaft of FIG. 34.

The second drive shaft 414, as best seen in FIGS. 34-36, is a single piece unit. Drive shaft 414 is shaped to have a cylindrical tail 416. Forward from tail 416 the drive shaft has a torso 420, also cylindrical in shape. The shaft torso 420 is coaxial with tail 416 and has an outer diameter greater than that of the tail. The second drive shaft 414 is further formed so that around the proximal end of the torso 420, where the torso extends radially beyond tail 416, there is an annular lip 418. Lip 418 extends circumferentially around drive shaft 414. The lip 418 projects radially beyond the outer surface of torso 420. As seen only in FIGS. 34 and 36, immediately rearward of the distal end of the torso 420, drive shaft 414 is formed to have a groove 422. Groove 422 extends inwardly from the outer surface of torso 420 and circumferentially around the torso.

A cylindrical head 426 extends forward from shaft torso 420. Head 426 is smaller in diameter than torso 420. Drive shaft 414 is shaped so that the head 426 is disposed on a longitudinal axis that is angularly offset from the common longitudinal axis of the shaft tail 416 and torso 420. Specifically, the shaft 414 has a neck 424 between the torso 420 and head 426. The neck 424 is circular in cross section and has a diameter between that of the torso 420 and head 426. The second drive shaft is further shaped so that the neck 424 has a distally directed face, not identified, that is in a plane not perpendicular to the common longitudinal axis of the shaft tail 416 and torso 420. Shaft head 426 extends from this face of the neck. The axis of the shaft head 26 where the head emerges from neck 424 is laterally offset from the longitudinal axis through the shaft tail 416 and torso 420. A groove 428 extends circumferentially around shaft head 426. Groove 428 is located a short distance rearward of the distal end of the head 426.

The second drive shaft 51 is further formed to have a closed end bore 430. Bore 430 extends distally forward from the proximal end of shaft tail 416. The bore 430 extends through tail 416 and partially through torso 420.

From FIG. 19 it can be seen that, during assembly of saw 230, gear 402 is mated to the second drive shaft 414. Specifically, the stem 408 of gear 402 is press fit into drive shaft bore 430. Gear 402 and the second drive shaft 414 can be considered a single-piece unit.

From FIG. 19 it is observed that, once the saw 230 is assembled, gear 402 and the second drive shaft 414 are positioned so that the gear and the portion of the shaft 422 that surrounds gear stem 408 are within void space 272 internal to saw neck 238. The shaft torso 422 is disposed in the neck void space 276. Bearing assemblies 434 and 440 rotatably hold the shaft torso 422 in the neck void space 276. (Not specifically illustrated are the inner and outer races of bearing assemblies 434 and 440.) The proximal of the two bearing assemblies, bearing assembly 434, is disposed over the proximal section of shaft torso 422. The inner race of bearing assembly 434 is seated against shaft lip 418.

Figure 21A:
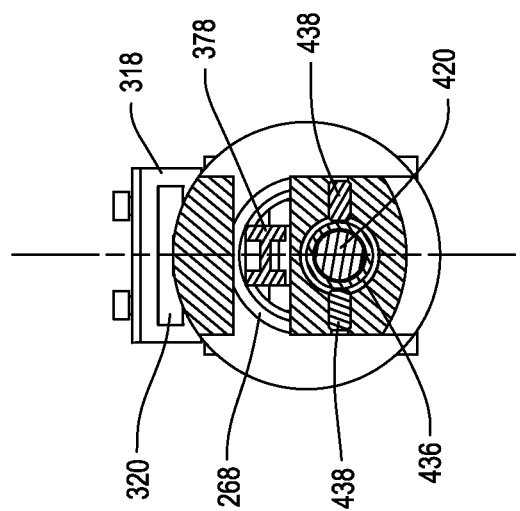
FIG. 21A is a cross sectional view of the saw head and blade mount taken along line 21A-21A of FIG. 19.

Immediately forward of bearing assembly 434 a sleeve 436 is disposed over the shaft torso 420. The sleeve 436 has a through bore, not identified, to accommodate the shaft torso 420. The sleeve 436 is not of constant diameter. Instead, the sleeve 436 is formed so that from each end of the sleeve the inner and outer walls of the sleeve taper inwardly. Thus the sleeve mid sections is of smaller diameter than the opposed ends of the sleeve 436. Sleeve 436 thus appears to have along the outer surface a circular channel that is centered on the midsection of the sleeve. The components forming saw 50 are arranged so that the outer ends of sleeve 436 bear against the inner cylindrical wall of the saw neck that defines bore 276. The sleeve mid section is spaced away from the drive shaft torso 420. Set screws 438 seen in FIG. 21A, are seated in the opposed ends of neck bore 277. The set screws 438 extend into neck void space 276 and the channel around the midsection of sleeve 436. The set screws 438 thus retain sleeve 436 and, by extension bearing assembly 434 from longitudinal movement within neck void space 276.

The distal bearing assembly, bearing assembly 440, is located over the distal section of the shaft torso 420 proximal to groove 422. A snap ring 442, seen only in FIG. 35, is seated in shaft groove 422. The inner race of bearing assembly 440 is seated against the portion of snap ring 442 that extends above the surface of the shaft torso 420. Snap ring 442 thus retaining bearing assembly 414 in neck void space 276 against the shaft torso 420.

Figure 18:
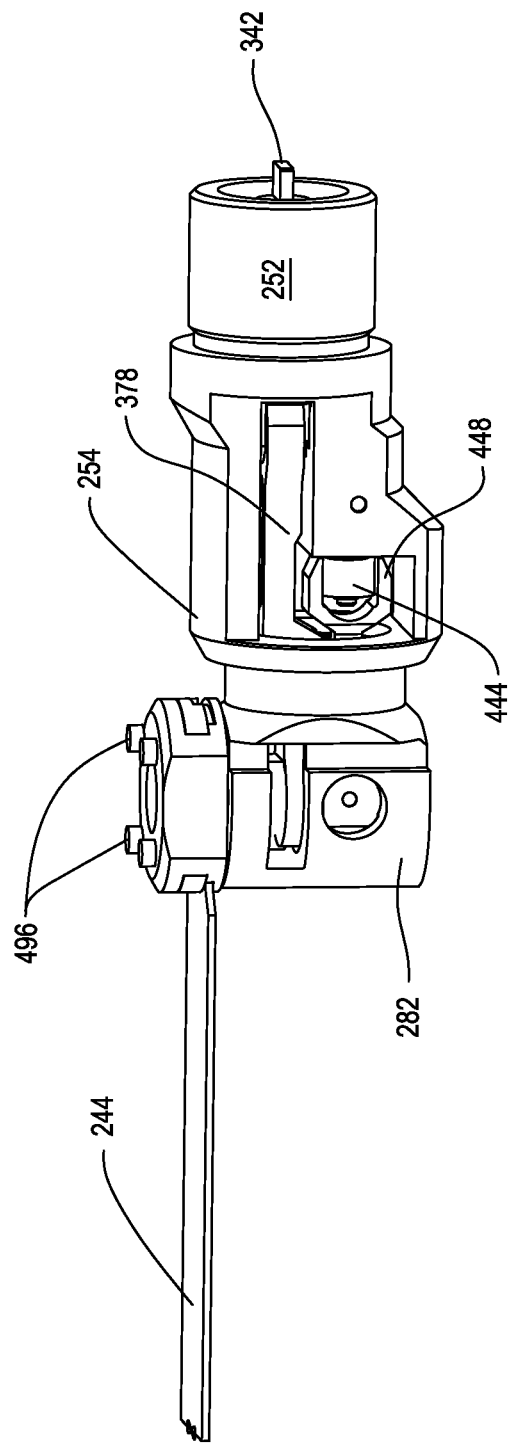
FIG. 18 is a plan view of the head and neck of the saw of FIG. 17 with a portion of the neck and head removed so as to show other components of the saw.

When the second drive shaft 414 is mounted in the saw neck 238, the shaft head 426 is disposed in the lower portion of the neck void space 270. A bearing assembly 444, seen best in FIGS. 18 and 39, is disposed over shaft head 426. A snap ring 446, identified only in FIG. 35, is seated in the groove 428 formed in the shaft head 426. The inner race of bearing assembly 444 is disposed between the shaft neck 424 and snap ring 446. While not explicitly illustrated, it should be understood that the bearing assembly 444 has an outer race with geometry of a slice section through a sphere.

Figure 37:
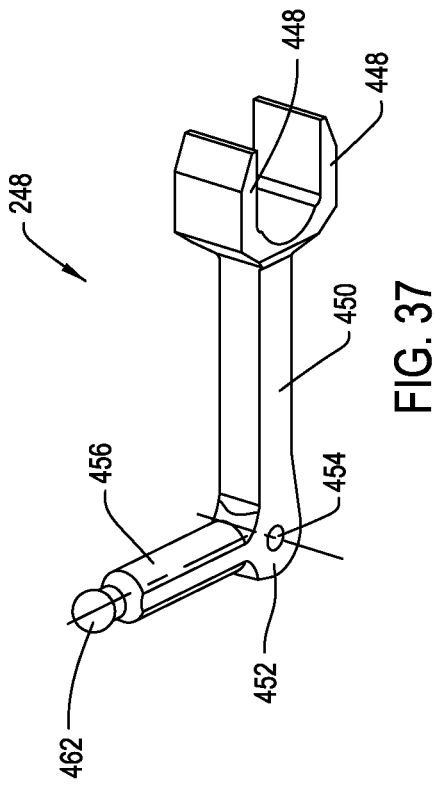
FIG. 37 is a perspective view of the toggle link of the surgical sagittal saw of FIG. 17.
Figure 38:
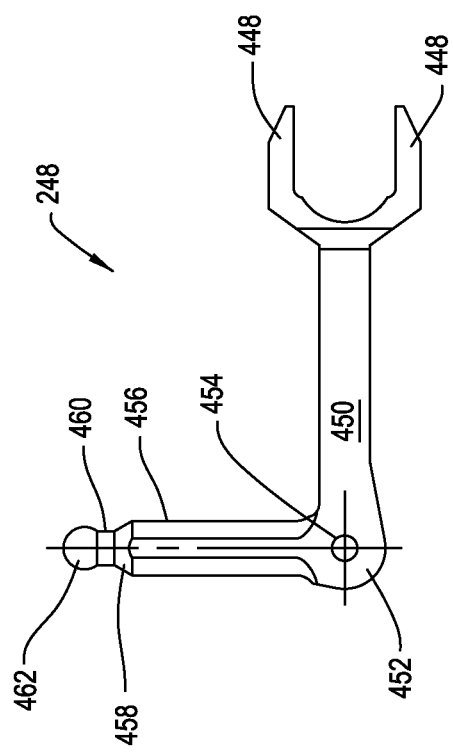
FIG. 38 is side view of the toggle link of FIG. 37

From FIGS. 37 and 38 it can be seen that the toggle link 248 is also a single piece component. The toggle link 248 is shaped to have two beams 450 and 456 that are perpendicular to each other. One beam, beam 450, as seen in the Figures, extends along a longitudinal axis that is generally horizontally aligned. Beam 450 has a generally rectangular cross sectional shape. Two spaced apart feet 448 extend proximally away from the proximal end of beam 448. Feet 448 are symmetrically located around the longitudinal axis that extend through beam 448 and are located above and below the axis. The toggle link 248 is shaped so that the feet 448 are spaced apart a distance that allows the outer race of bearing assembly 444 to closely fit there between. As is discussed below, when saw 230 is actuated, link feet 448 and beam 450 pivot in and out of the plane of FIG. 38. The feet 448 have a width, the distance in the plane in and out FIG. 38, greater than that of beam 450. More particularly, the width of the feet 448 is such that, regardless of the angular displacement of the feet, bearing assembly 444 will remain disposed between the feet.

The illustrated toggle link 248 is formed so that there is a hub 452 at the most distal end of beam 450. The hub 452 has an arcuate outer surface. In the vertical plane of FIG. 38, hub 452 projects beyond the underside surface of beam 450. The hub 452 is formed to have a through bore 454. Bore 454 extends side-to-side through the hub 452. Bore 454 is centered around the axis around which the front and downwardly directed outer surface of hub 452 curves.

The second toggle link beam, beam 456, extends upwardly from hub 452. Beam 456 is centered a longitudinal axis that is perpendicular to the longitudinal axis of hub bore 454. The beam 456 is formed so as to have curved front and rear surfaces and planar side surfaces (surfaces not identified). the front-to-back distance across beam 456 is greater than the side-to-side thickness of the beam. The front to back width of beam 456 is less than the diameter of blade mount bore 324. Immediately above beam 456, the toggle link 248 has a shoulder 458 that tapers inwardly from front, rear and side surfaces of the beam. A cylindrical neck 460 extends upwardly from shoulder 458. The toggle link 248 also has a head 462 disposed above neck 460. Head 462 is spherical in shape. The diameter across the head 462 is greater than the diameter across the adjacent neck 460. More particularly the toggle link 248 is shaped so that head 462 projects beyond neck 460 but is located inwardly of the area subtended by beam 456.

Upon assembly of saw 50, the toggle link 248 is positioned so that the feet 448 seat over bearing assembly 444. Beam 450 extends through head sleeve bore 281. Hub 452 is disposed in blade mount notch 302. Beam 456 extends through blade mount bores 324 and 326 and partially through bore 328. The toggle link 248 is further dimensioned so that the link head 462 projects into the blade mount slot 320.

A pin 466, identified only in FIGS. 21B and 39, pivotally connects the toggle link 248 to the blade mount 242. The pin 466 is seated in the bore 454 that extends through link hub 452. The ends of pin 466 extend beyond the toggle link 248. The ends of the pin 466 seat in the opposed ends of bore 310 in the blade mount stem 298. The toggle link 248 is thus mounted to the blade mount 242 to both pivot with the blade mount and toggle back and forth within the blade mount. The distal portion of the hub 452, the portion of toggle link 248 that extends forward of beam 456 extends into the window 308 formed in the blade mount stem 298.

It should likewise be understood the beam 450 of toggle link 248 is disposed under beam 382 of drive link 246. Consequently, as illustrated by FIG. 39, the tabs 390 integral with the drive link 246 are disposed around the opposed sides of toggle link beam 450. The drive link 246 and toggle link 248 are collectively shaped so that the width across toggle link beam 450 is such that the toggle link beam is slip fit between the drive link tabs 390.

As seen by reference to FIG. 40, when saw 230 is readied for use, the blade 244 is positioned so that the proximal end of the blade is seated in the base of blade mount slot 320, between steps 322. The width of this portion of blade 244 seated in the blade mount 242 is less than the width between the opposed faces of the blade mount steps 322. A wear bar 480 is disposed between each blade mount step 322 and the adjacent side of the blade 244. The wear bars 480 are formed from metal such as carbide so as to resist galling.

The structure of a wear bar 480 is now described by reference to FIG. 41. The bear includes a center beam 482. Beam 482 has a rectangular cross sectional shape. A tab 484 extends away from the end of each beam 482. Each pair of tabs 484 integral with a beam 482 have inwardly directed surfaces (surfaces not identified). These inwardly directed surfaces that are directed towards each other are parallel to each other and perpendicular to the longitudinal axis through the beam 482. Each tab 484 also has an outwardly directed surface (surfaces not identified). The outwardly directed surfaces extend laterally away from the associated beam 482 and curve towards and meet the adjacent inner surface. Collectively, each wear bar 480 is shaped so that when the beam is placed adjacent the associated blade mount step 322, the tabs 484 extend outwardly, away from the front to rear longitudinal axis through the blade mount slot 320. Each wear bar tab 484 extends over one end of the adjacent blade mount step 322.

Figure 44:
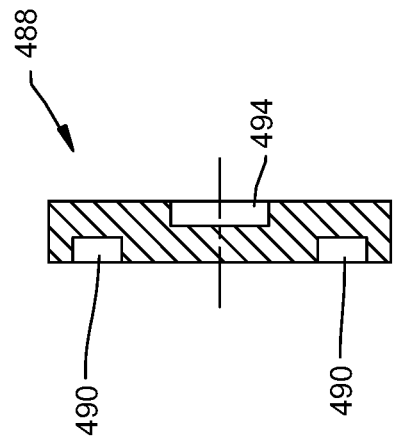
FIG. 44 is a cross sectional view of the lock plate taken along line 44-44 of FIG. 42.
Figure 42:
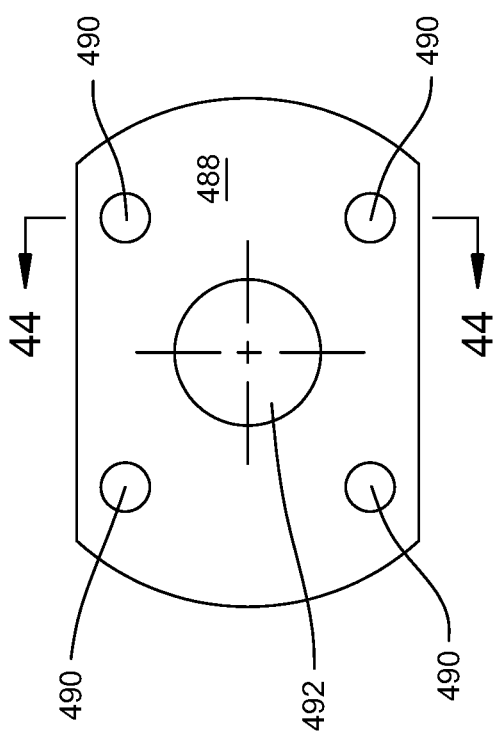
FIG. 42 is a top plan view of the lock plate internal to the blade mount.
Figure 43:
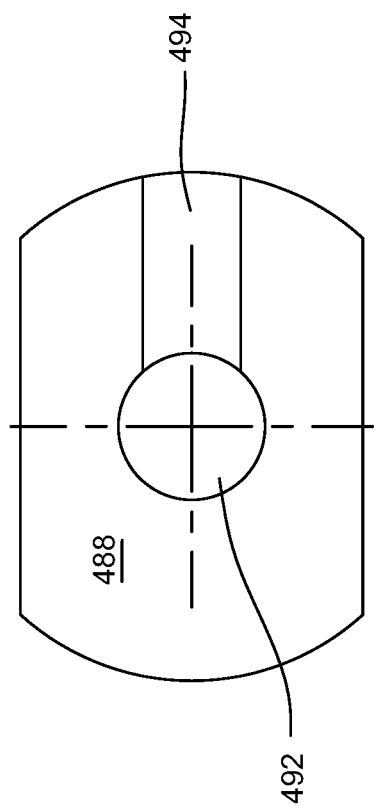
FIG. 43 is a bottom plan view of the lock plate.

A lock plate 488, shown in detail in FIGS. 42-44, is disposed in blade mount slot 320 to removably hold the blade 244 to the blade mount 244. The lock plate 488 has outwardly curved front and rear faces and parallel side faces (faces not identified). Lock plate 488 is designed to slip fit in blade mount slot 320 above steps 322. The lock plate 488 is further shaped so that, when seated in the blade mount slot 320, the lock plate front and rear faces are generally even with the adjacent front and rear faces of the blade mount 320. Four closed end bores 490 extend inwardly from the top surface of the lock plate. Bores 490 are positioned so that when the lock plate 488 is seated in the blade mount slot 320, each bore 490 is in registration under one of the threaded bores 330 that extends inwardly from the top of the blade mount head 318.

Lock plate 488 is further formed to have a through bore 492. The lock plate 488 is shaped so that when the plate is held to the blade mount head 318, through bore 492 is concentric with blade mount bore 328. In one version of the invention through bore 492 has a diameter less than that of blade mount bore 492. The lock plate 488 also has a slot 494 that extends inwardly from the undersurface of the plate, the surface directed towards blade mount steps 322. Slot 494 extends distally away from bore 492 to the rearwardly directed face of the plate 488.

Four thread fasteners 496, identified only in FIG. 18, hold the lock plate 488 in the blade mount slot 320. Each fastener 496 is threaded in one of the blade mount bores 330. Each fastener 496 extends into one of the plate bores 490.

Figure 45:
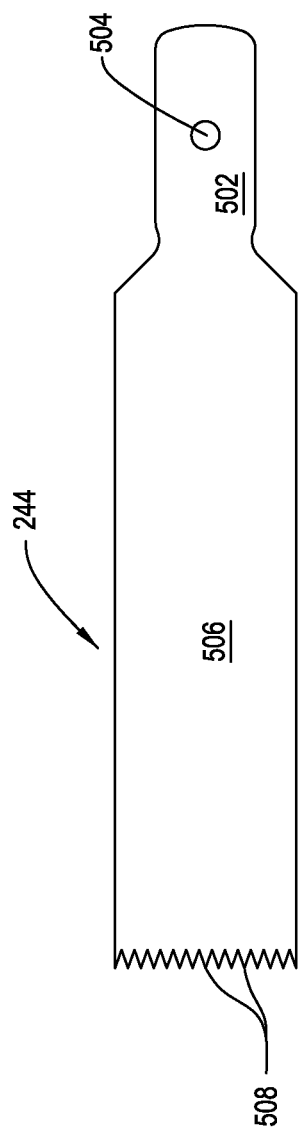
FIG. 45 is a plan view of a blade used with the surgical sagittal saw of FIG. 17.

A blade 244 of this invention is now described by reference to FIG. 45. Blade 244 is generally planar in shape. The blade has a proximal or tail section 502. The blade tail section 502 has a width that allows the tail section to closely fit between the spaced apart wear bars 480. A through hole 504 extends through opposed top and bottom surfaces of the tail section. The blade 244 is shaped so that when the blade is seated in the blade mount slot 322, toggle link head 462 will seat in hole 504. Through hole 504 has a diameter that allows the toggle link head 462 to closely and slidably fit in the hole 504.

Forward of tail section 502, blade 244 has a main section, section 506. In the depicted version of the invention, main section has a width across greater than that of the tail section 502. This feature is not necessary all versions of the invention. The blade main section 506 may have a width less than or equal to that of the tail section 502. When the blade main section 506 is of greater width than the tail section, the sides of the blade taper outwardly between the sections, (side taper not identified). This side taper limits the extent to which the blade tail 502 can be inserted in blade mount slot 320. The blade main section 506 has a distal end (not identified). The blade teeth 508 extend forward from the distal end of the blade main section.

Saw 230 of this invention is readied for use by placing the blade in the blade mount slot 329 as seen in FIG. 40. At this time the wear bars 480 are disposed on either side of the blade tail section 502. The toggle link head 462 is disposed in the blade hole 504. A portion of the toggle link head 462 extends above the top surface of the blade 244. Lock plate 488 is then slid in blade mount slot 320 above the blade tail section 502. The presence of slot 494 internal to the lock plate 494 allows the plate to be slid over and around the toggle link head 462. Fasteners 496 are then screwed into the top of blade mount head 318. The ends of the fasteners 496 press against the surfaces of the lock plate 488 that define the bases of bores 490. Fasteners 496 thus hold the lock plate 488 in the blade mount slot 320. Lock plate 488 thus constrains the blade from significant vertical movement up or down in the slot 320. This vertical constraint prevents the blade from moving above toggle link head 462. If such movement was possible, the blade once so lifted, could be pulled out of the blade mount 242. While lock plate 488 is disposed over the blade tail section 502, steps 322 suspend the lock plate 488 above the tail. Thus, while the lock plate 488 prevents removal of the blade 244 from the blade mount 242, the plate does restrict the forward and back, (distal and proximal) movement of the blade within blade mount slot 320.

To actuate saw 230 of this version of this invention, trigger 64 is depressed. The depression of trigger 64 causes the control module to actuate the motor 60. The motor actuates the output shaft so as to cause the first drive shaft 340 to rotate. The rotation of the first drive shaft 340 causes the shaft nose 356 and bearing 388 to turn in a circle around the longitudinal axis of the shaft 340. Bearing 388 actually rotates within neck void space 266. Owing to the attachment of drive link 246 to bearing 388, the rotation of the bearing results in the pivoting of the proximal end of the drive link. This displacement of the drive link 246 causes the link to pivot the blade mount 242. Specifically, the blade mount is pivoted around the longitudinal axis through the blade mount stem 298. Since blade 244 is attached to the blade mount 242, the blade undergoes a like pivotal motion. Further, since the toggle link 248 is attached to the blade mount 242 the toggle link engages in the same pivotal motion.

The rotation of the first drive shaft 340 does more than pivot blade mount 242 and the attached saw blade 244. Gear teeth 352 of the first drive shaft 340 are engaged with the gear teeth of gear 402. Thus, the rotation of first drive shaft 340 causes gear 402 the attached second drive shaft 414 to rotate. Owing to the 2:1 ratio between the gear teeth on the first drive shaft 340 to the teeth of gear 402, gear 402 and the second drive shaft 414 rotate at twice the speed of the first drive shaft 340. The rotation of the second drive shaft 414 results in the shaft head 426 rotating in a circle around the longitudinal axis through the shaft 414. Owing to the connection of the toggle link 248 to the shaft head 414 by bearing 444, the circular movement of the shaft head 444 causes the attached end of toggle link beam 450 to pivot up and down. This pivoting motion is around the longitudinal axis through bore 454 internal link hub 452. The up and down pivoting of the link beam 450 is converted through hub 452 to motion that causes link beam 456 to pivot forward and rearwardly. Toggle link head 462, attached to the end of beam 456 therefore undergoes this same repetitive forward/rearward/forward/rearward repetitive motion. Since the blade 244 is closely mated to the toggle link head 462 and is able to move back and forth in the blade mount slot 320, the blade is forced to undergo the same repetitive back and forth motion.

Thus, simultaneously, while the blade mount 242 pivots the blade to the left and right of the front-to-rear longitudinal axis through the saw head 240, the toggle link 248 reciprocates the blade back and forth along the longitudinal axis of the blade 244. Since the toggle link 248 moves at twice the frequency at which drive link 246 pivots the blade mount, a tooth on blade 244 transits the same loop pattern depicted in FIG. 16 as a tooth of blade 52 attached to saw 50.

When saw 230 is actuated, the pivoting of the blade mount 242 results in a like pivoting of toggle link beam 450. During a sweep of this pivoting motion, the angular momentum of the section of the beam 450 spaced from the blade mount 242 is greater than that of section closer to the mount. Owing to this difference in momentum, at the times the beam 450 undergoes a directional reversal, there can be a lag in the movement of the section of the beam spaced from the blade mount 242 in comparison to the section closest to the blade mount. This lag, essentially a bending of the beam, induces stress in the beam. Over time, this stress could cause the beam to fracture.

Saw 230 of this invention is, however, constructed so toggle link beam 450 is located between the drive link tabs 390. Consequently, tabs 390 force the underlying section of the toggle link beam 450 to undergo the same right to left and back pivotal motion as the drive link 246. The section of the toggle link beam 450 spaced away from the blade mount therefore essentially rotates in synchronization with the portion of the beam closest to the blade mount 242. This feature of this invention thus eliminates the lag in the pivotal movement of the toggle link 248 that can potentially be a source of fracture inducing stress.

III. Alternative Embodiments

It should be appreciated that the foregoing is directed to specific embodiments of this invention. Other versions of the invention may have features different from what has been described.

For example, this invention is not limited to battery powered saws or saws with electric motors. Some saws of this invention may have electric motors that are driven by energization signals supplied from control consoles over cables that extend to the saw. Still other saws of this invention may include pneumatic or hydraulic motors. While not illustrated, some saws may include reduction gear assemblies. These assemblies reduce the rotational speed/increase the output of the torque the motor outputs to the shaft used to actuate the saw drive assembly.

Likewise, the shape of the saw may vary from what has been described and illustrated. Thus, instead of having a saw with a pistol shaped body, the saw may be pencil like, in the form of an elongated cylinder. This is especially true of what are referred to as micro-sagittal saws. These saws have blades that may have a width across of 1.5 cm or less.

Similarly there is no requirement that in all versions of the invention the ratio of the frequency with which the saw blade is reciprocated distally and proximally to the frequency with which the blade is pivoted to the right and left be the 2:1 ratio of the described versions of the invention. In some versions of the invention it may even be desirable to pivot the blade to the right and left at a frequency greater than the frequency with which the blade is reciprocated distally and proximally. For example, if the blade is pivoted right and left at a frequency that is two times the frequency with which the blade is reciprocated distally and proximally, the blade teeth will engage in the loop of travel depicted in FIG. 46. In this embodiment invention, the blade teeth are pivoted right to left to right against the tissue which they are applied. Then in the next phases of cycle the blade teeth are retracted from the face of the uncut tissue. During the retraction phase of the cycle the bleed teeth are again pivoted right to left to right. The retraction phase of the cycle facilitates the clearance of the cut debris away from the face of the uncut tissue.

Figure 46:
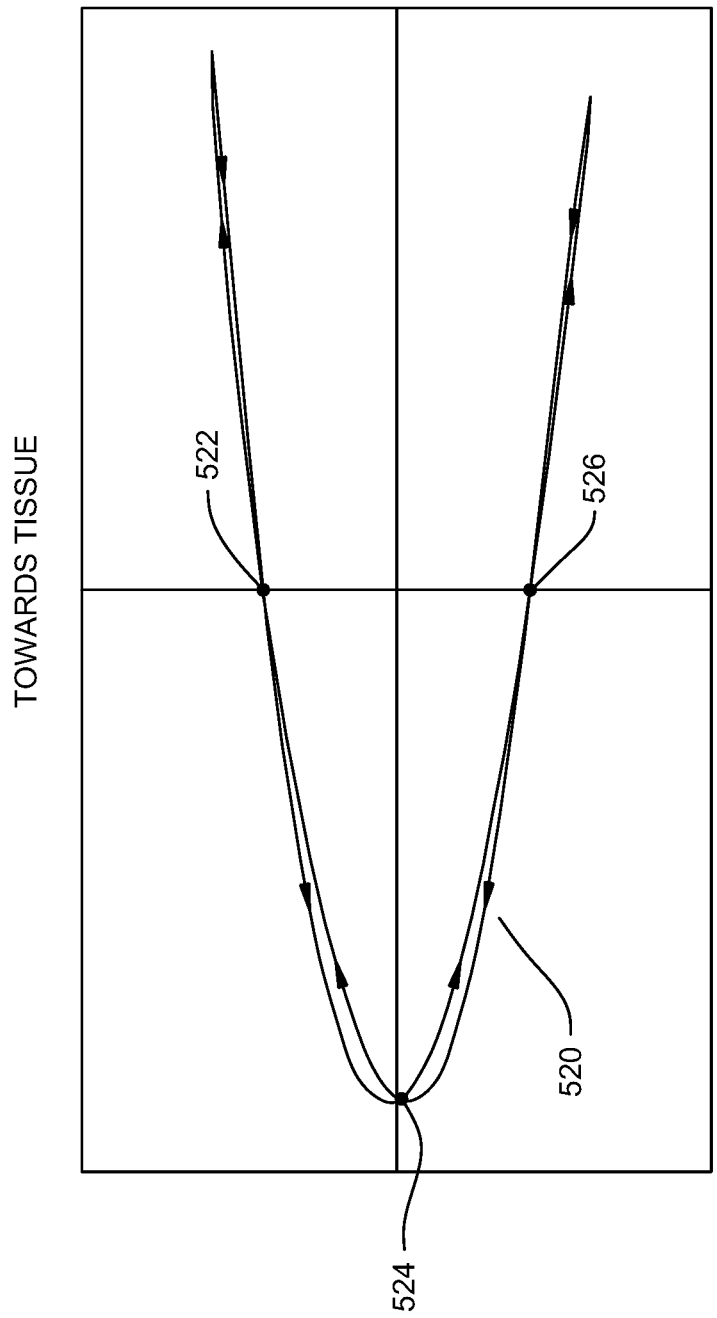
FIG. 46 depicts an alternative path of travel loop a blade tooth may undergo with an alternative saw of this invention.

It should be appreciated that, with changes in the ratio between the pivotal and reciprocal displacement of the blade, the pattern of travel of the blade teeth will change. Depending on the relative frequencies of blade displacement, the blade tooth as it cycles through a single loop 520 of displacement may even cross over plural segments of the loop over which it previously traveled. This is illustrated in the loop pattern of FIG. 46 where there are three points 522, 524 and 526 in the loop of travel of the tooth, the tooth crosses over previous points of travel. FIG. 46 also illustrates that there is no requirement that, in all constructions of this invention that one of the loop cross over points intersect the extension of the longitudinal axis of the blade. Further, there is no requirement that the loop pattern be symmetric relative to the longitudinal axis of the blade. Though, however, such symmetry is believed to be preferred.

Furthermore, the relative phases of the pivotal right to left and back movement and reciprocating front to rear and back movement of the actuating members may be varied. For example, in the described embodiments, the phasings of these actuating members is such that when the blade tooth is in the center of a front to back (or back to front reciprocation) it is also in the center of a right to left (or left to right) pivotal sweep. Other phasings of the blade actuating members may be possible.

Further, the blade head and components that displace the blade may be able to index relative to the body of the saw. One such indexing mechanism is disclosed in the Applicants' Assignee's PCT Pub. No. WO 2007/011542A1 also published as US Pat. Pub. No. 2007/0016238 A1, the contents of which are incorporated herein by reference. Likewise, there is no requirement that in all versions of the invention, the blade mount be attached to a head that is separate from the saw body.

It should similarly be appreciated that the components of the drive assembly that pivot and reciprocate the blade are different from what has been described. For example, in some versions of the invention, one or more of the drive assembly components may be a bearing assembly. An outer race of this bearing assembly is what is disposed against and displaces the blade. When the bearing assembly is itself displaced, the outer race rotates relative to the center of the assembly. An advantage of this construction is that the outer race of the bearing assembly is less prone to wear than a static pin. Further, it should be understood that in some versions of the invention the blade mount that holds the blade may be the drive assembly that reciprocates back and forth. The second drive assembly is a pin or bearing that, when actuated pivots the blade relative to the mount.

In still other versions of the invention, none of the actuating members may directly work against the blade. In these versions of the invention, the actuating members may both displace the blade mount, the assembly to which the blade is attached. A first one of these actuating members pivots the blade mount to the right and left of a longitudinal axis of the static member of the saw to which the blade mount is attached. The second actuating member simultaneously reciprocates the blade mount between distal and proximal positions along the static member. Since the blade is rigidly attached to the blade mount, the blade therefore undergoes the like motion.

In version of the invention wherein the blade mount functions as one of the drive members that displaces the blade, this mount may not always be the component that pivots the blade. In some versions of the invention, the blade mount may reciprocate the blade back and forth along the longitudinal axis of the saw. A drive pin mounted to the blade oscillates back and forth over an arc. This drive head functions as the component that pivots the blade.

Alternative means may also be used to hold the blade to the blade mount. For example a pin may be mounted to the blade mount to move up or down relative to the surface of the mount on which the blade is seated. The pin may have a head disposed above the blade mount that is dimensioned to extend over a portion of the blade. The blade may have an opening in which the pin can move yet of smaller width across than the width across the pin head. Thus the pin constrains the blade from movement away from the blade mount while allowing the blade to move longitudinally (or pivotally) over the blade mount.

In some constructions of the invention, while the blade may pivot around an axis that extends through the plane in which the blade is oriented, this axis may not be perpendicular to this plane.

Likewise, it should be understood that geometry of blade teeth may be different from what has been described. The distal end of the blade may even be formed with one or more openings between the teeth.

The blade may have different features than what has been described. For example blade openings 178, 180 and/or 182 may be sections of a larger single opening. There is no requirement that in all versions of the invention, openings 178 and 182 have major axes that are in registration with the longitudinal axis through the blade. In some versions of the invention, these axis may only be offset from and substantially parallel to the longitudinal axis along the blade. Here "substantially" parallel to the longitudinal axis means that if the axes intersect, they intersect at an angle of 45° or less. Likewise, the opening 180 need not always be symmetric with and have a major axis that is perpendicular to the longitudinal axis along the blade 52. In some versions of the invention the major axes of opening 180 need only be substantially perpendicular to the longitudinally axis along the blade. Here "substantially" perpendicular is understood to mean that these axes intersect at an angle of at least 45°.

Likewise blade 52 may be formed with a feature other than opening 178 that engages a static component of the saw in order to constrain movement of the blade. These feature me be one or more indentations formed in the side, or opposed sides of the blade.

Also, there is no requirement that in all versions of the invention the constraining feature, opening 178, always be located distally forward of the openings 180 and 182 that receive, respectively, drive pins 106 and 120. Likewise, there is no requirement that the opening 180 that receives drive pin 106 always be located proximal to the opening 182 that receives drive pin 182. The proximal-to-distal orientations of these features may be shifted from what is described.

Therefore, it is the goal of the appended claims to cover all such modifications and variations that come within the true spirit and scope of this invention.

What is claimed is:

1. A surgical sagittal saw, said saw including:
    a body;
    a motor disposed in said body, said motor having an output shaft that is rotated upon actuation of said motor;
    a blade mount attached to said body that is configured to releasably receive a surgical sagittal saw blade, the saw blade having a distal end with teeth;
    a drive assembly connected between said motor output shaft and the saw blade, said drive assembly including first and second actuating members that engage the saw blade, wherein:
        said first actuating member is configured to undergo a motion that reciprocates the saw blade back and forth in a plane in which the blade is disposed;
        said second actuating member is configured to undergo a motion that pivots the saw blade back and forth around an axis that extends through the plane in which the saw blade is reciprocated; and
    said first and second actuating members are connected to said motor output shaft so that the rotation of said output shaft causes said actuating members to simultaneously reciprocate and pivot the saw blade such that the saw blade reciprocates at a first frequency and pivots at a second frequency that is different from the first frequency.

2. The surgical sagittal saw of claim 1, wherein said drive assembly first and second actuating members are connected to said motor output shaft to reciprocate and pivot the saw blade at different frequencies so the teeth of the blade travel in a loop pattern that crosses over itself at at least one point.

3. The surgical sagittal saw of claim 1, wherein:
a longitudinal axis extends between opposed proximal and distal ends of said body; and
said drive assembly first and second actuating members are further connected between said motor output shaft and the saw blade to reciprocate and pivot the saw blade so the teeth of the saw blade move in a loop pattern that crosses over itself at a point along an extension of the longitudinal axis that extends between opposed proximal and distal ends of said body.

4. The surgical sagittal saw of claim 1, wherein said drive assembly first and second actuating members are further connected between said motor output shaft and the saw blade to reciprocate and pivot the saw blade at different frequencies so that the teeth of the blade travel in a loop pattern that crosses over itself at at least one point and that is symmetric around at least one axis that extends through the loop.

5. The surgical sagittal saw claim 1, wherein said drive assembly first and second actuating members are further connected between said motor output shaft and the saw blade to reciprocate and pivot the saw blade at different frequencies so that the teeth of the blade travel in a loop pattern that crosses over itself at a single point.

6. The surgical sagittal saw claim 1, wherein said blade mount is moveably attached to said body and is part of said drive assembly such that the blade mount is able to move so that the movement of said blade mount results in at least one of the reciprocating movement or pivoting movement of the saw blade.

7. The surgical sagittal saw of claim 1, wherein:
said blade mount is moveably attached to said body and is part of one of said drive assembly first or second actuating members such that the movement of said blade mount results in one of the reciprocating movement or pivoting movement of the saw blade; and
said drive assembly includes a drive link that is moveably mounted to said blade mount that is part of the other one of said drive assembly second or first actuating members and that is shaped to engage the saw blade and the movement of which results in the other of the pivoting movement or reciprocating movement of the saw blade.

8. The surgical sagittal saw of claim 7, wherein:
said blade mount is moveably mounted to said body to pivot the saw blade; and
said drive assembly drive link mounted to said blade mount is moveably mounted to said blade mount to reciprocate the saw blade.

9. The surgical sagittal saw of claim 1, wherein said at least one of said drive assembly first or second actuating members is formed with a pin that is shaped to engage the saw blade and said pin is mounted to said body to pivot back and forth around an axis.

10. The surgical sagittal saw of claim 1, wherein at least one of said drive assembly first or second actuating members is mounted to said body to rotate in a complete 360° circle.

11. The surgical saw of claim 1, wherein said blade mount includes:
a surface on which the blade is seated for moveable movement; and
a static component mounted to the surface that engages the saw blade to constrain movement of the blade on the surface.

12. The surgical sagittal saw of claim 1, wherein:
the saw blade is moveably mounted to said blade mount; and a wear bar is removably mounted to said blade mount so as to be between the blade and an adjacent static feature of said blade mount.

13. The surgical sagittal saw of claim 1, wherein said drive assembly first and second actuating members are connected to said motor output shaft and are configured to reciprocate the saw blade at frequency that is greater than the frequency at which the saw blade is pivoted.

14. The surgical sagittal saw of claim 1, wherein said drive assembly first and second actuating members are connected to said motor output shaft and are configured to reciprocate the saw blade at a frequency that is two times the frequency at which the saw blade is pivoted.

15. The surgical saw of claim 1, wherein said blade mount is mounted to a head that is located forward of said body.

16. The surgical saw of claim 1, further including a cap that is moveably disposed over said blade mount to removable hold the saw blade to said blade mount.

17. The surgical sagittal saw of claim 1, wherein:
said first actuating member includes a first coupling feature that releasably engages the saw blade so that the motion of said first actuating member results in the reciprocation of the saw blade; and
said second actuating member includes a second coupling feature separate from said first coupling feature that releasably engages the saw blade so that the motion of said second actuating member results in the pivoting of the saw blade.

18. The surgical sagittal saw of claim 1, wherein:
a single one of said first actuating member or said second actuating member is connected to said motor output shaft for actuation upon the rotation of said output shaft; and
the other of said second actuating member or said first actuating member is connected to the said actuating member connected to said motor output shaft for actuation upon the actuation upon the actuation of said actuating member connected to said output shaft.

19. The surgical sagittal saw of claim 1, wherein at least one of said drive assembly first actuating member or said second actuating member is a drive shaft that is connected to said motor output shaft to, upon rotation of said output shaft, rotate.

20. The surgical sagittal saw of claim 1, wherein:
said drive assembly first actuating member is a first drive shaft that is rotatably mounted to said body;
said drive assembly second actuating member is a second drive shaft separate from said first drive shaft that is rotatably mounted to said body; and
both said first and second drive shafts are connected to said motor output shaft to, upon rotation of said output shaft, rotate.

21. A surgical sagittal saw said saw including:
a body;
a motor disposed in said body, said motor having an output shaft that is rotated upon actuation of said motor;
a blade mount attached to said body that is configured to releasably receive a surgical sagittal saw blade, the saw blade having a distal end with teeth;
a first drive member moveably mounted to said body and that is positioned to engage the saw blade so that movement of said first drive member causes said first drive member to reciprocate the saw blade back and forth relative to said blade mount in a plane in which the saw blade is disposed;
a second drive member moveably mounted to said body and that is separate from said first drive member, said second drive member being configured and positioned to engage the saw blade so that the movement of said second drive member causes said second drive member to pivot the saw blade around an axis that extends through the plane in which the saw blade is disposed; and a transmission assembly connected between, at one end, said motor output shaft and, at a second end, to said first drive member and said second drive member, said transmission assembly configured to transfer the movement of said motor output shaft to said drive members so that said first drive member undergoes a repetitive movement at a first frequency and said second drive member undergoes a repetitive movement at a second frequency different from the first frequency.

22. The surgical sagittal saw of claim 21, wherein said first drive member, said second drive member and said transmission assembly are collectively configured so that the simultaneous reciprocation of the saw blade by said first drive member and pivoting of the saw blade by said second drive member results in the saw blade traveling in a loop pattern that crosses over itself at at least one point.

23. The surgical sagittal saw of claim 21, wherein said transmission assembly is connected to at least one of said first drive member or said second drive member to cause said drive member to repetitively rotate through a 360° circle.

24. The surgical sagittal saw of claim 21, wherein said transmission assembly is connected to both said first drive member and said second drive member to cause each said drive members to both repetitively rotate through 360° circles.

25. The surgical sagittal saw of claim 21, wherein said transmission assembly includes: a first gear attached to said motor output shaft; and a second gear attached to at least one of said first drive member or said second drive member that engages said first gear so as to be rotated upon the rotation of said motor output shaft.

26. The surgical sagittal saw of claim 21, wherein said transmission assembly includes: a first gear attached to said first drive member; and a second gear attached to said second drive member wherein said first and second gear are engaged so that the rotational movement of one said drive member results in the rotational movement of the other said drive member.

27. The surgical sagittal saw of claim 21, further including a static member mounted to said blade mount, said static member positioned to engage a section of the saw blade so as to constrain the movement of the saw blade relative to said blade mount.

28. The surgical sagittal saw of claim 21, wherein said first drive member, said second drive member and said transmission assembly are collectively configured so that when said drive members undergo movement, said first drive member reciprocates the saw blade at a frequency that is greater than the frequency at which said second drive member pivots the saw blade.

29. The surgical sagittal saw of claim 21, wherein said blade mount is disposed in a head that is located forward of said body.

30. A surgical sagittal saw said saw including:
a body;
a motor disposed in said body, said motor having an output shaft that is rotated upon actuation of said motor;
a blade mount moveably mounted to said body that is configured to releasably receive a surgical sagittal saw blade, the saw blade having a distal end with teeth, wherein said blade mount is moveably mounted to said body so that movement of said blade mount that results in the attached saw blade undergoing one of: a reciprocating movement wherein the saw blade moves back in and forth in a plane in which the saw blade is disposed; or a pivoting movement in which the saw blade pivots around an axis that extends through the plane in which the saw blade is disposed; and a first drive link that is mounted to said blade mount and configured to engage the saw blade, wherein said first drive link is moveably mounted to said blade mount and so that the movement of said first drive link results in said first drive link causing the saw blade to engage in the other one of: the pivoting movement; or the reciprocating movement; and a drive assembly located between, at one end, said motor output shaft and, at an opposed end, said blade mount and said first drive link, said drive assembly configured to transfer the rotation of said motor output shaft to said blade mount and said first drive link so that said blade mount and said first drive link engage in simultaneous movement that results in the saw blade undergoing reciprocating movement at a first frequency and pivoting movement at a second frequency that is different from the first frequency.

31. The surgical sagittal saw of claim 30, wherein:
said blade mount is mounted to said body and said drive assembly is connected to said blade mount so that the rotation of said motor output shaft results in said blade mount pivoting the saw blade; and
said drive link is mounted to said blade mount and said drive assembly is connected to said drive link so that the rotation of said motor output shaft results in said drive link reciprocating the saw blade.

32. The surgical sagittal saw of claim 30, wherein said drive assembly includes a second drive link that is separate from said first drive link, said second drive link connecting the motor output shaft to said blade mount so that the rotation of said motor output shaft is transferred through said second drive link to said blade mount to move said blade mount.

33. The surgical sagittal saw of claim 30, further including at least one wear bar removably mounted to said blade mount so as to be located between the saw blade and a static feature of said blade mount.

34. The surgical sagittal saw of claim 30, wherein:
said blade mount is formed to define a slot dimensioned to receive the saw blade; and
said first drive link extends into the blade mount slot to engage the saw blade.

35. The surgical sagittal saw of claim 30, wherein:
said blade mount is formed to define a slot dimensioned to receive the saw blade; and
a plate is removably secured in the blade mount slot and configured to removably hold the saw blade in the blade mount slot so the saw blade can move in the slot.

36. The surgical sagittal saw of claim 30, wherein said drive assembly, said blade mount and said first drive link are collectively configured so that when said blade mount and said first drive link simultaneously reciprocate and pivot the saw blade, the saw blade is reciprocated at a frequency greater than the frequency at which the saw blade is pivoted.

37. The surgical sagittal saw of claim 30, wherein said drive assembly, said blade mount and said first drive link are collectively configured so that when said blade mount and said first drive link simultaneously reciprocate and pivot the saw blade, the saw blade travels in a loop pattern that crosses over itself at at least one point.

38. The surgical sagittal saw of claim 30, wherein said drive assembly, said blade mount and said first drive link are collectively configured so that when said blade mount and said first drive link simultaneously reciprocate and pivot the saw blade, the saw blade travels in a loop pattern that crosses over itself at a single point.

\* \* \* \* \*